US011432806B2

(12) United States Patent
Baba et al.

(10) Patent No.: US 11,432,806 B2
(45) Date of Patent: Sep. 6, 2022

(54) INFORMATION PROCESSING APPARATUS, INFORMATION PROCESSING METHOD, AND STORAGE MEDIUM

(71) Applicant: CANON KABUSHIKI KAISHA, Tokyo (JP)

(72) Inventors: Yoshitaka Baba, Tokyo (JP); Kenichi Nagae, Yokohama (JP); Yukio Furukawa, Sagamihara (JP); Kouichi Kato, Yokohama (JP); Hiroshi Abe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 125 days.

(21) Appl. No.: 16/735,498

(22) Filed: Jan. 6, 2020

(65) Prior Publication Data
US 2020/0222029 A1 Jul. 16, 2020

(30) Foreign Application Priority Data

Jan. 11, 2019 (JP) .............................. JP2019-003584

(51) Int. Cl.
A61B 8/08 (2006.01)
A61B 8/14 (2006.01)
G06T 7/00 (2017.01)

(52) U.S. Cl.
CPC .......... *A61B 8/5269* (2013.01); *A61B 8/0833* (2013.01); *A61B 8/14* (2013.01); *A61B 8/5246* (2013.01); *G06T 7/0014* (2013.01); *G06T 2207/30004* (2013.01)

(58) Field of Classification Search
CPC ......... G06T 7/0014; G06T 2207/30004; A61B 8/5269; A61B 8/0833; A61B 8/14; A61B 8/5246
See application file for complete search history.

(56) References Cited

U.S. PATENT DOCUMENTS

| 2012/0310086 A1 | 12/2012 | Fukumoto |
| 2013/0245418 A1 | 9/2013 | Oishi |
| 2013/0245419 A1 | 9/2013 | Oishi |
| 2013/0261427 A1 | 10/2013 | Oishi |

(Continued)

FOREIGN PATENT DOCUMENTS

WO 2016129376 A1 8/2016

*Primary Examiner* — Amelie R Davis
*Assistant Examiner* — John Denny Li
(74) *Attorney, Agent, or Firm* — Canon U.S.A., Inc. I.P. Division

(57) ABSTRACT

An information processing apparatus includes an image data acquisition unit and a template data acquisition unit. The image data acquisition unit acquires a plurality of pieces of image data generated by performing a plurality of ultrasonic wave transmission and reception operations on a subject while changing an ultrasonic wave transmission and reception mode. The template data acquisition unit acquires a plurality of pieces of template data corresponding to the plurality of ultrasonic wave transmission and reception operations, respectively. The similarity information acquisition unit acquires information indicating a similarity between an image value sequence of the plurality of pieces of image data at a target position and a template data sequence of the plurality of pieces of template data at the target position.

15 Claims, 11 Drawing Sheets

(56) References Cited

U.S. PATENT DOCUMENTS

2013/0336088 A1* 12/2013 Umezawa ............ A61B 5/0095
                                                    367/8
2015/0011882 A1*  1/2015 Abe .................... G01S 15/8995
                                                    600/443

* cited by examiner

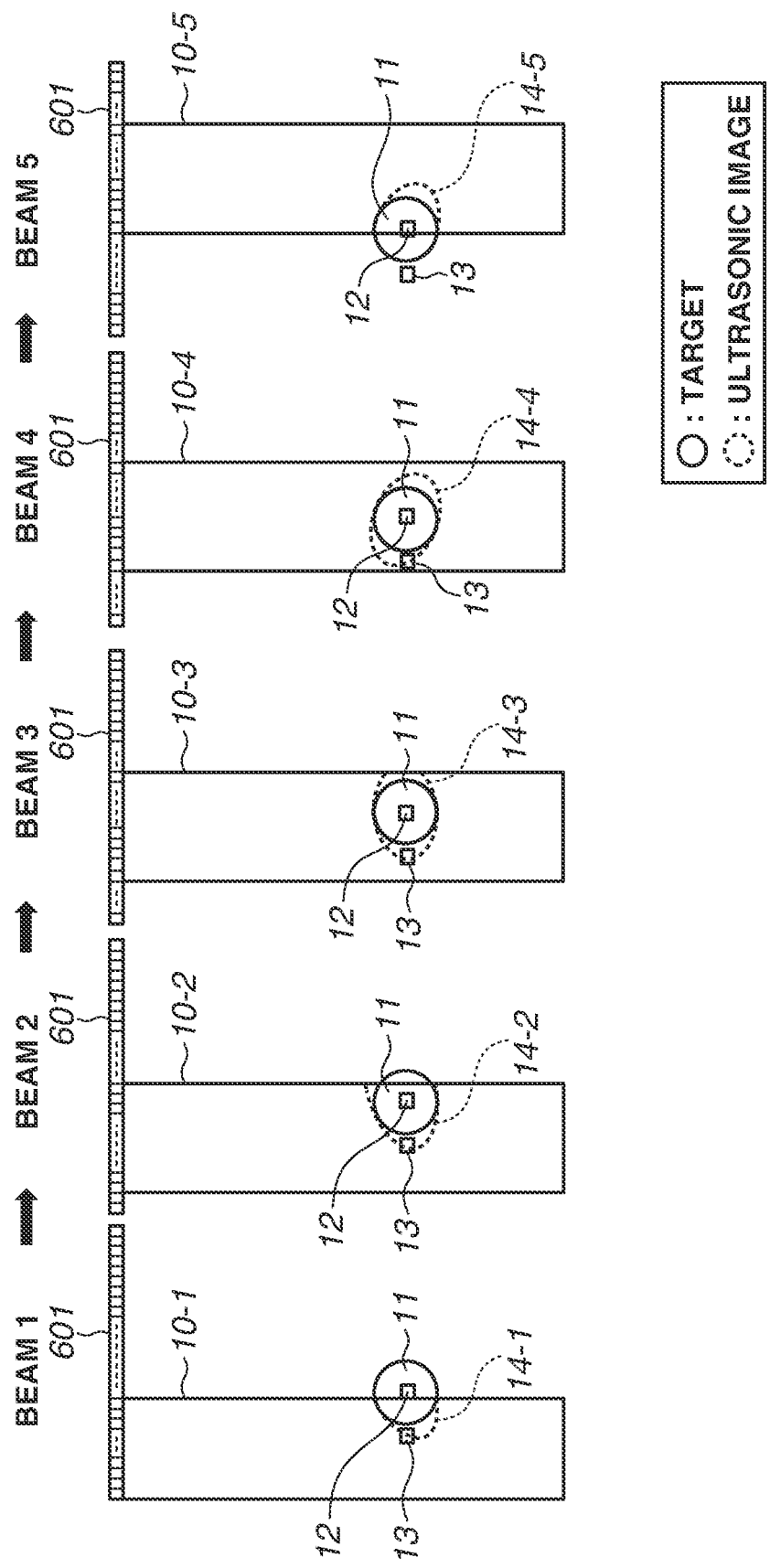

HIGH CORRELATION: TARGET IS PRESENT

LOW CORRELATION: TARGET IS NOT PRESENT

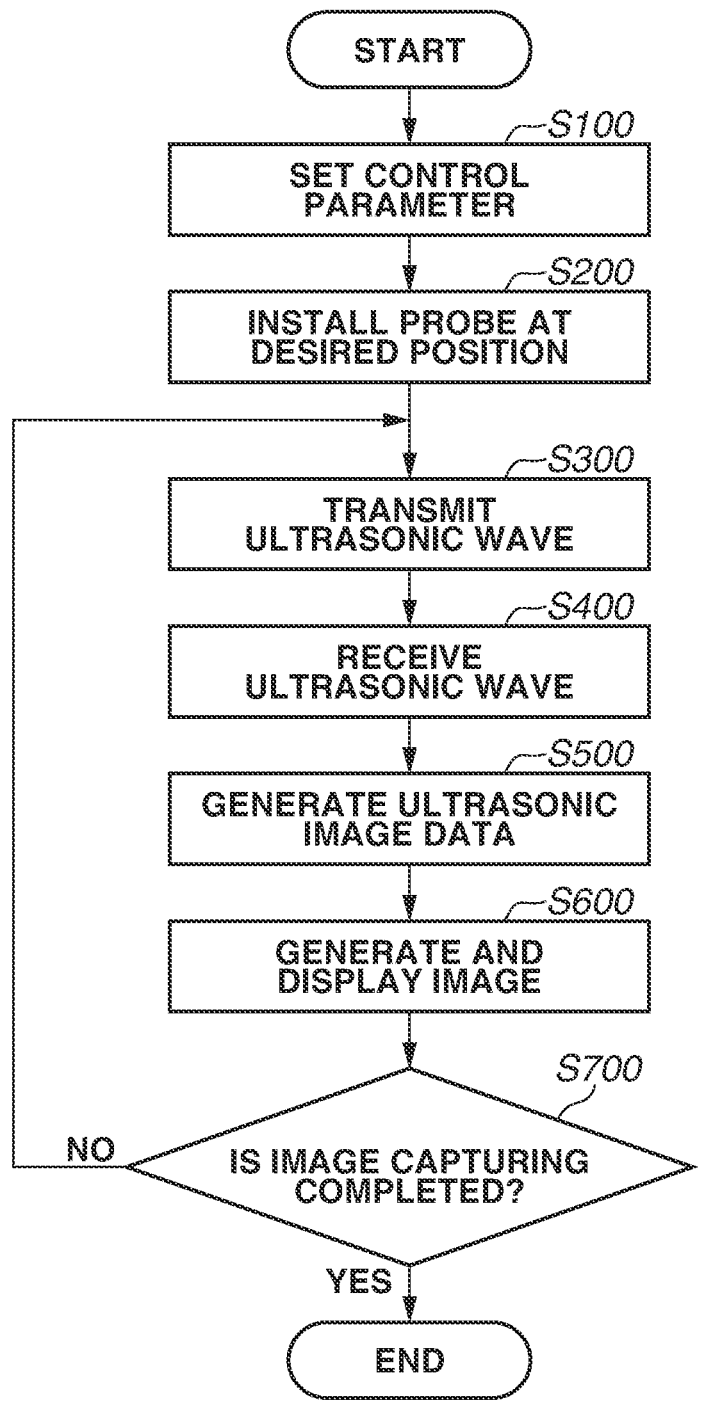

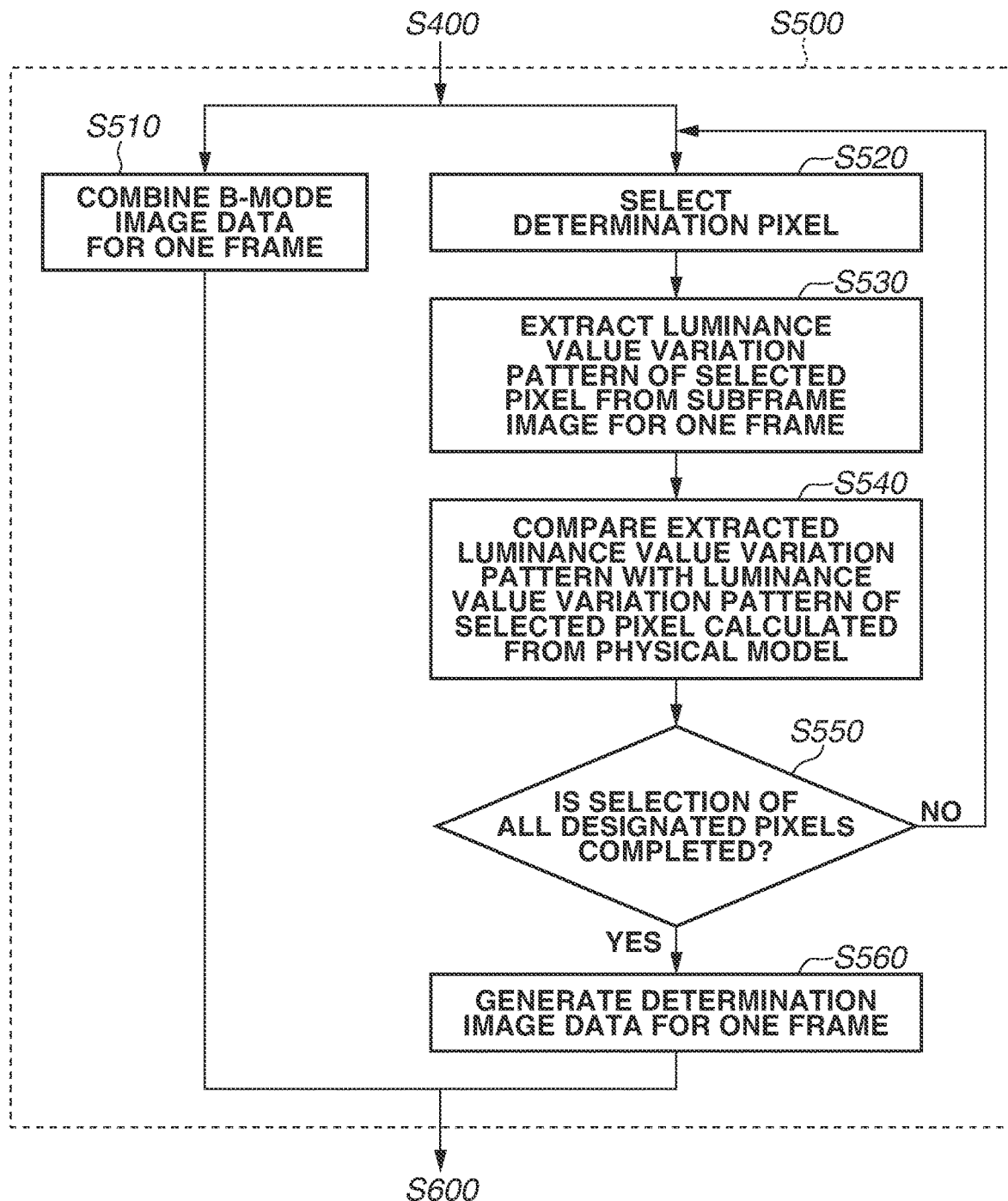

INFORMATION PROCESSING APPARATUS, INFORMATION PROCESSING METHOD, AND STORAGE MEDIUM

BACKGROUND

Field

The present disclosure relates to an information processing technique for processing image data generated by transmitting and receiving an ultrasonic wave.

Description of the Related Art

Conventionally, an ultrasonic diagnostic apparatus uses a technique called electronic scanning method in which an ultrasonic wave is transmitted to the inside of a subject, in particular, a living body, and a reflection echo that is reflected inside the living body and returned is received with high accuracy.

In such an ultrasonic diagnostic apparatus, an ultrasonic beam is transmitted and received by a one-dimensional or two-dimensional probe in which a plurality of micro transducers is arranged. In the case of transmitting an ultrasonic beam, delay circuits are used to set variable timings for voltage application to each micro transducer so that a scanning direction of the ultrasonic beam can be changed, and the ultrasonic beam performs scanning while a delay time for each delay circuit is sequentially changed. In recent years, an ultrafast method in which a width of an ultrasonic beam to be transmitted once is increased and a plane wave is used, or techniques similar to the ultrafast method have attracted attention because a frame rate of an ultrasonic image can be increased.

International Patent Publication No. WO 2016/129376 discusses a technique for reducing artifacts by multiplying a unique weighting coefficient for each pixel and combining the calculation results by using a plurality of ultrasonic images acquired by increasing the width of an ultrasonic beam at an opening of each of different ultrasonic probes.

According to the technique discussed in International Patent Publication No. WO 2016/129376, an artifact may be included in an ultrasonic image, which makes it difficult to determine whether a target (observation target) is present at a target position in the image.

SUMMARY

The present disclosure is directed to an information processing apparatus that acquires information allows easy determination of whether the possibility is high or low that a target (observation target) is present at a target position in an image.

According to an aspect of the present disclosure, an information processing apparatus includes an image data acquisition unit configured to acquire a plurality of pieces of image data generated by performing a plurality of ultrasonic wave transmission and reception operations on a subject while changing an ultrasonic wave transmission and reception mode, a template data acquisition unit configured to acquire a plurality of pieces of template data corresponding to the plurality of ultrasonic wave transmission and reception operations, respectively, and a similarity information acquisition unit configured to acquire information indicating a similarity between an image value sequence of the plurality of pieces of image data at a target position and a template data sequence of the plurality of pieces of template data at the target position.

Further features of the present disclosure will become apparent from the following description of exemplary embodiments with reference to the attached drawings.

BRIEF DESCRIPTION OF THE DRAWINGS

FIG. 4 illustrates an operation status in which an ultrasonic image is generated according to the first exemplary embodiment.

FIG. 7 is a flowchart illustrating an operation flow to be performed by the processing apparatus according to the first exemplary embodiment.

FIG. 8 is a flowchart illustrating an operation flow of an image generation method according to the first exemplary embodiment.

DESCRIPTION OF THE EMBODIMENTS

Figure 1:
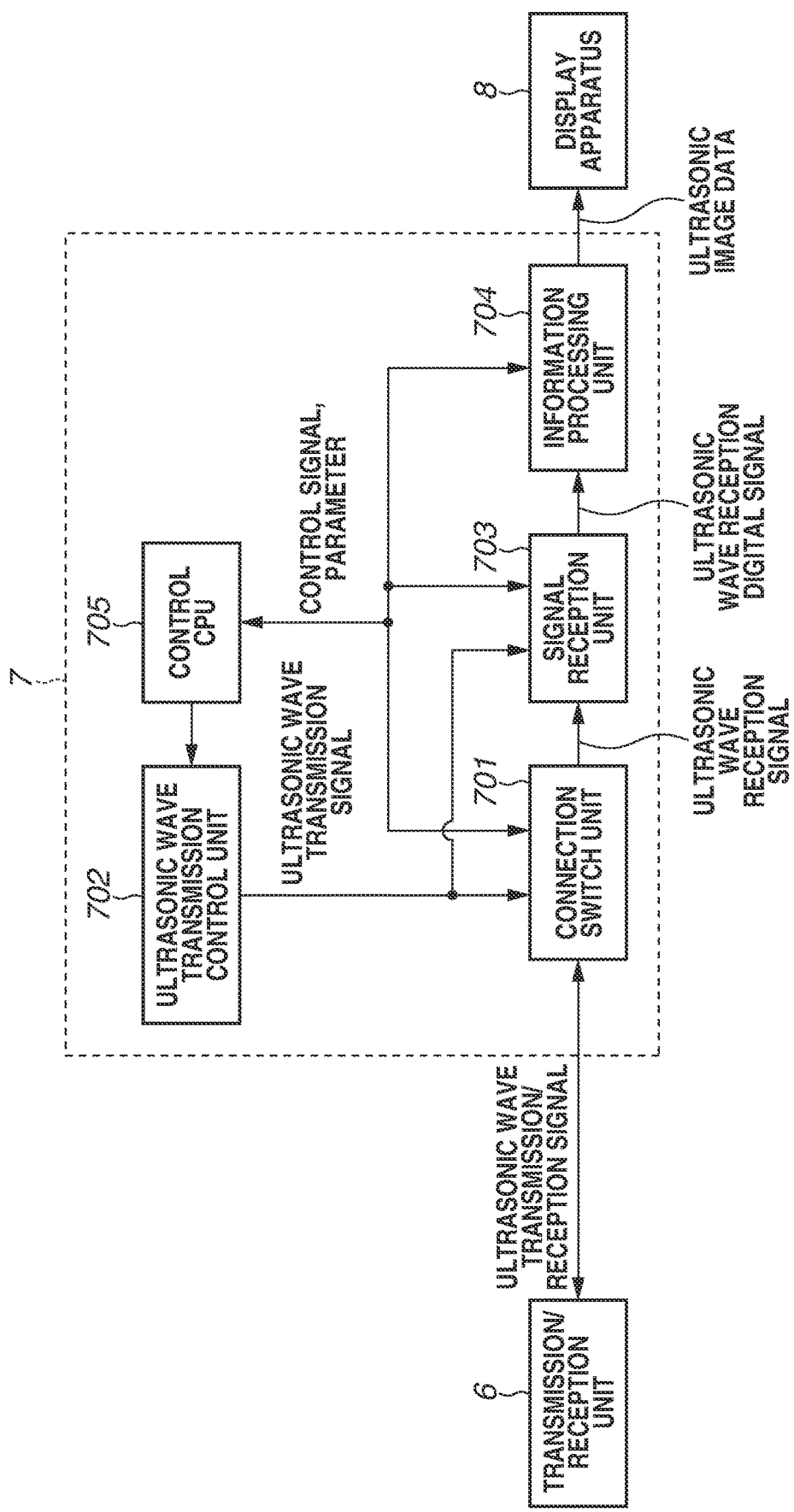
FIG. 1 is a block diagram strafing a processing apparatus according to a first exemplary embodiment.

Exemplary embodiments of the present disclosure will be described below with reference to the accompanying drawings. The dimensions, materials, and shapes of components described in the following exemplary embodiments, the relative arrangement of the components, and the like should be appropriately modified in accordance with the configuration of an apparatus to which the present disclosure is applied and various conditions, and the scope of the present disclosure is not limited to the following exemplary embodiments.

The present disclosure relates to a technique for generating image data representing a two-dimensional or three-dimensional spatial distribution derived from ultrasonic waves transmitted to a subject and reflected inside the subject. Ultrasonic image data is image data representing a spatial distribution of subject information, such as a distribution of scattering substances with different acoustic impedances in the subject.

A living body, which is a main subject for ultrasonic wave imaging, has a characteristic for reflecting and scattering an ultrasonic wave. Scattering of an ultrasonic wave causes image noise called speckles in an ultrasonic image. Speckles may provide a clue to the properties of a living body tissue, while speckles deteriorates the visibility of the living body tissue in the ultrasonic image.

As discussed in International Patent Publication No. WO 2016/129376, artifacts caused when signals are reinforced by a phase addition method at a location where a target is not actually present appear in an ultrasonic image. As a result, an image quality such as a contrast may deteriorate due to artifacts, which are caused by the presence of a target, in the case of imaging a living body tissue present in a subject. This may make it difficult to determine whether an image in the ultrasonic image corresponds to a target (observation target) image.

By an information processing apparatus and an information processing method according to a first exemplary embodiment, it is possible to easily determine whether a target (observation target) is present at a certain position in an image. In other words, by the information processing apparatus and the information processing method of the present exemplary embodiment, it is possible to easily determine whether it is more easily determined whether a possibility of a target being present at a certain position in an image is high. Herein, determining whether a target is present is equivalent to determining whether the possibility of the presence of the target is high. Processing according to the present exemplary embodiment will be described below.

FIG. 4 illustrates an example in which a plurality of ultrasonic wave transmission operations is performed on a subject and an ultrasonic image is generated in a certain area. Ultrasonic wave transmission beams 10-1 to 10-5 are transmitted from a probe array 601. A target 11 is present in an area of an ultrasonic image generation target. Assume that N elements 601-1 to 601-N are present in the probe array 601.

FIG. 4 is a conceptual diagram illustrating artifacts 14-1 to 14-5 caused by the presence of the target 11 when the ultrasonic wave transmission beams 10-1 to 10-5 each having a width in the direction of the probe array 601 are transmitted. As illustrated in FIG. 4, the artifacts 14-1 to 14-5 appear differently depending on a positional relationship between the ultrasonic wave transmission beams 10-1 to 10-5 and the target 11.

Figure 5A:
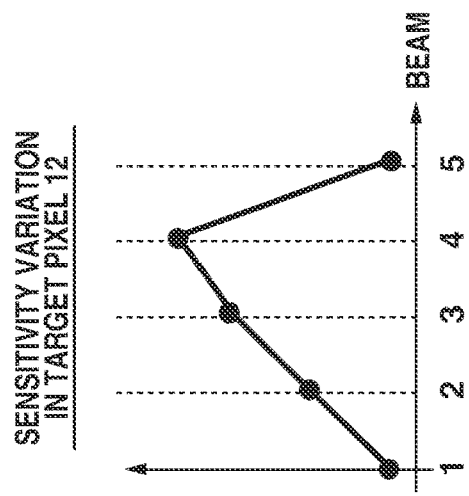
FIGS. 5A, 5B, 5C, and 5D are graphs each illustrating a luminance value variation and a sensitivity variation according to the first exemplary embodiment.
Figure 5B:
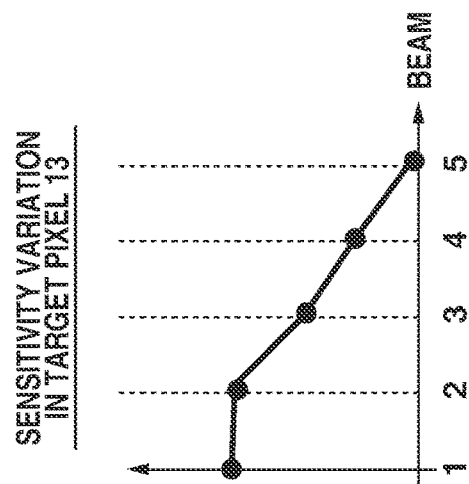

In the present exemplary embodiment, luminance values of the ultrasonic wave transmission beams 10-1 to 10-5 in pixels 12 and 13 illustrated in FIG. 4 are compared. FIG. 5A is a graph illustrating a luminance value variation in the pixel 12 corresponding to the inside of the target 11. FIG. 5B is a graph illustrating a luminance value variation in the pixel 13 corresponding to the outside of the target 11.

In the pixel 12 corresponding to the inside of the target 11, the luminance value varies depending on the positional relationship between the pixel 12 and the ultrasonic wave transmission beams 10-1 to 10-5. In the case of the ultrasonic wave transmission beam 10-1 illustrated in FIG. 4, the pixel 12 is located at an end of the beam, and thus a reflected ultrasonic wave signal has a low intensity. As a result, the luminance value obtained when imaging is performed using the phasing addition method decreases. In the case of the ultrasonic wave transmission beams 10-2 to 10-5, the luminance value obtained when imaging is performed using the phase addition method increases as the pixel 12 approaches the center of the beam.

Figure 5C:
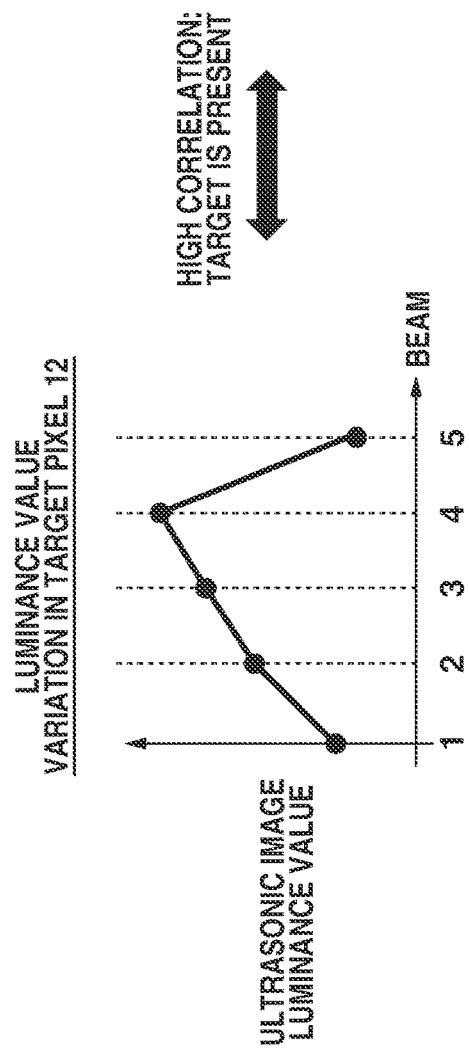

As a result, if the number of each of the ultrasonic wave transmission beams 10-1 to 10-5 is plotted on an X-axis and the luminance value of the pixel 12 obtained when imaging is performed using the phase addition method is plotted on a Y-axis, luminance value variation characteristics as illustrated in FIG. 5C are expressed as a graph. This is an example where an ultrasonic wave transmission beam is formed so that a transmission sound pressure of ultrasonic wave transmission at the center of the beam becomes higher than that at an end of the beam.

In general, a physical model representing ultrasonic wave transmission and reception characteristics is expressed by sophisticated mathematical expressions and is highly systemized. Accordingly, if a scattering substance that reflects an ultrasonic wave is present at the position of the pixel 12, a variation of the luminance value of the pixel 12 can be calculated in advance by the phase addition method.

Figure 6:
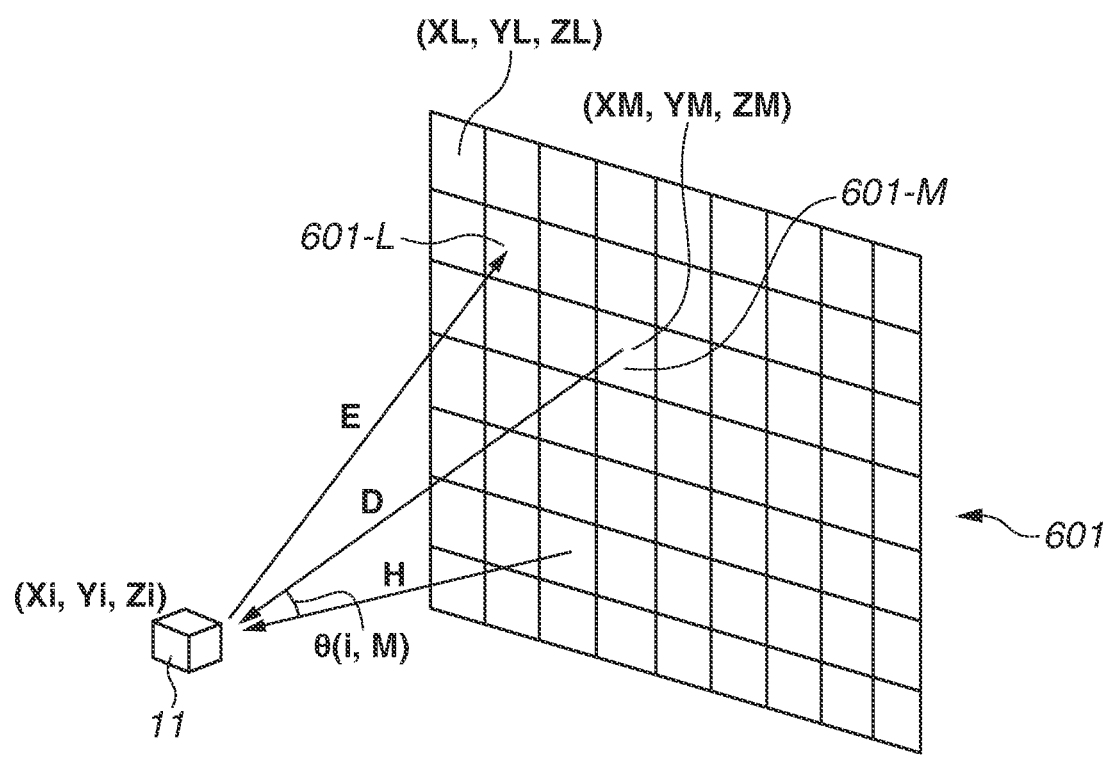
FIG. 6 illustrates a directionality of a probe array according to the first exemplary embodiment.

For example, assume a case where, if the element 601-M (M=1 to N) in the probe array 601 illustrated in FIG. 6 emits an ultrasonic wave having an amplitude AM and a frequency FM in a direction indicated by a normal vector H, the element 601-N has a rectangular shape. In this case, a directionality with respect to a pixel 11-$i$ ($i$=1 to T) located at a position in a direction in which an angle $\theta$ (i, M) is formed with the normal vector H is represented by the following expression (1):

$$R\theta(i,M)=|\sin(k\alpha \sin \theta(i,M))/k\alpha \sin \theta(i,M)| \quad (1)$$

where $k=2\pi$ FM/sound speed, and a=element pitch/2.

For example, a sound pressure P (i, M) in the pixel 11-$i$ ($i$=1 to T) of the ultrasonic wave transmitted by the element 601-M is represented by the following expression (2):

$$P(i,M)=\alpha(i,M) \times A_M \times R\theta(i,M) \quad (2)$$

where $\alpha$ (i, M) is a coefficient representing an attenuation received from a medium by an ultrasonic wave propagating from the element 601-M (M=1 to N) to the pixel 11-$i$ ($i$=1 to T) and mainly dependent on subject properties and the frequency FM.

If a scattering substance having the same size as the pixel 11-$i$ ($i$=1 to T) is present at the position of the pixel 11-$i$ ($i$=1 to T), the scattering substance reflects the ultrasonic wave, and a reflected wave, that is, an ultrasonic echo signal propagates in the direction of the probe array 601. In this case, for example, when the reflected wave reaches the element 601-L (L=1 to N), a sound pressure $P_{array}$(i, L, M) of the reflected wave derived from the scattering substance is represented by the following expression (3).

$$P_{array}(i,L,M)=\beta(i,L) \times \Gamma(i) \times P(i,M) \times \text{Selectric}(L) \times \text{Sspatial}(i,L) \quad (3)$$

In the expression (3), $\beta$(i, L) represents a coefficient representing an attenuation given on the ultrasonic echo signal due to the propagation of the ultrasonic wave through the medium, and is mainly dependent on tissue properties of the subject and the frequency FM. $\Gamma$(i) represents a reflectance when the ultrasonic wave signal is reflected by the scattering substance present in the pixel 11-$i$. $S_{electric}$(L) represents a conversion efficiency of the element 601-L. In other words, $S_{electric}$(L) is a parameter indicating a correspondence relationship with the intensity of an electric signal output from the element 601-L when the element 601-L receives the ultrasonic wave. $S_{spatial}$(i, L) represents a spatial impulse response of the element 601-L, that is, the directionality of the element 601-L in the direction of the pixel 11-$i$.

Assume a case where the ultrasonic echo signal obtained when ultrasonic beams transmitted using T elements in the probe array 601 are reflected by the scattering substance present in the pixel 11-$i$ is received using the T elements in the probe array 601. In this case, a sound pressure value $P_{array}$(i) obtained when a reception signal of an ultrasonic wave echo is added is represented by the expression (4).

In other words, the sound pressure value $P_{array}$(i) is a value obtained by superimposing the value represented by the expression (3) on all the transmission elements 601-M and reception elements 601-L. This is a concept used in a method generally called a Synthetic Transmit Aperture (STA) method.

$$P_{array}(i) = \sum_{M=1}^{N} \sum_{L=1}^{N} P_{array}(i, L, M) \quad (4)$$

Assume a case where a scattering substance is present at a specific pixel position in an image capturing target area. In this case, the ultrasonic wave echo that propagates from the scattering substance and is obtained from the ultrasonic wave transmitted from a certain element 601-M (M=1 to N) in the probe array 601 is received by the element 601-L (L=1 to N), and a signal value obtained by adding the ultrasonic wave echo can he calculated. The "signal value obtained by adding the ultrasonic wave echo" is hereinafter referred to as a "luminance value".

Further, luminance value information about a set of pixels 11-$i$ (i=1 to T) in an image capturing area when the ultrasonic wave transmission operation is performed using the probe array 601 can be obtained by the following expression (5):

$$P_{array\_total} = \sum_{i=1}^{T} \sum_{M=1}^{N} \sum_{L=1}^{N} P_{array}(i, L, M) \quad (5)$$

In the expressions (2) and (4), an apodization coefficient is not multiplied by the element 601-L (L=1 to N) and the element 601-M (M=1 to N). However, a calculation model in which an apodization coefficient is taken into consideration may be used.

The expressions (1) to (5) use the concept of the STA method that is generally used for beam forming in ultrasonic image capturing. This results in realizing the phase addition method in which a transmission focus and a reception focus are in focus on each pixel 11-$i$ (i=1 to T).

However, the beam forming processing that is applicable to the present disclosure is not limited to this method. A calculation model corresponding to other beam forming methods can also be used.

For example, assume a case where a luminance value for each pixel 11-$i$ (i=1 to T) is calculated when a transmission beam focused on a certain area in the image capturing area. In this case, the luminance value may be calculated by correcting the term P(i, M) in the expression (3) in consideration of a delay time of each element 601-M (M=1 to N) for focusing the transmission beam.

In this way, the luminance value adaptable to various transmission beam focusing modes and reception beam focusing modes can be calculated. In other words, the luminance value of the pixel 11-$i$ (i=1 to T) that is adaptable to various beam foaming methods can be calculated. Changing at least one of the transmission beam focusing mode and the reception beam focusing mode is equivalent to changing the ultrasonic wave transmission and reception mode. The ultrasonic wave transmission and reception mode may be changed by a method other than the method of changing the transmission or reception beam focusing mode. For example, the ultrasonic wave transmission and reception mode may be changed by changing a direction of transmitting an ultrasonic wave as a plane wave.

The luminance value may be calculated by a simulator using a method such as a k-wave method.

$\alpha(i, M)$, $\beta(i, L)$ and $\Gamma(i)$ are parameters that are affected by the tissue properties of the subject. Accordingly, it is desirable to set an optimum parameter to an image capturing target depending on the subject and to use the optimum parameter for calculation.

Further, $S_{electric}(L)$ represents an electric performance of an element used for a probe of a subject information acquisition apparatus. Accordingly, the characteristics of a representative element may be applied to all elements, or individual characteristics may be assigned to respective elements.

In general, characteristics indicated by $S_{spatial}(i, L)$ vary depending on the shape, such as a circular shape or a rectangular shape, of an element, and thus optimum characteristics may be desirably assigned to the shape of respective elements to be used.

A mode for adjusting the parameters may be provided exclusively for the subject information acquisition apparatus according to the present exemplary embodiment so that an optimum value can be set for each of the parameters by using a test phantom or the like.

FIG. 5B illustrates an example of a graph in which a variation of the luminance value derived from the pixel 12 is calculated in advance by the above-described method using the phase addition method and the calculated variation is plotted when the ultrasonic wave transmission beams 10-1 to 10-5 are transmitted.

As seen from a comparison between FIGS. 5A and 5B, luminance value variation characteristics illustrated in FIG. 5A are similar to those illustrated in FIG. 5B.

Figure 5D:
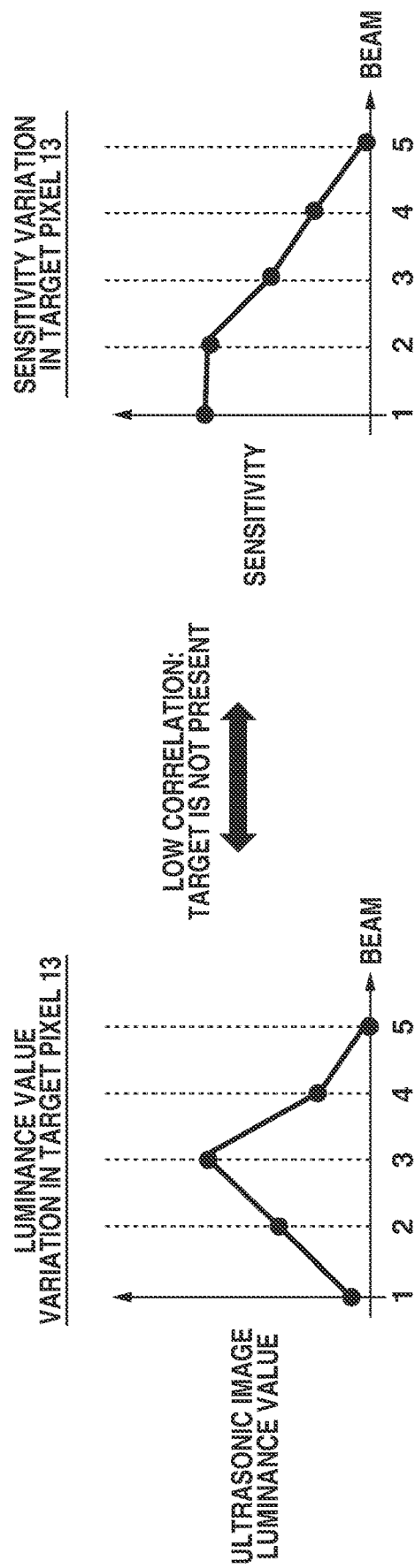

FIG. 5C illustrates luminance value variation characteristics in the pixel 13 corresponding to the outside of the target 11. FIG. 5D illustrates an example of a result of a preliminarily calculated luminance value variation in the pixel 13 in accordance with a physical model representing ultrasonic wave transmission and reception characteristics. No scattering substance is present in a portion corresponding to the pixel 13, and thus it is estimated that a variation or the like does not occur in the luminance value. However, in practice, a variation of the luminance value occurs due to the artifacts 14-1 to 14-5 caused by the presence of the target 11. As a result, a luminance value variation as illustrated in FIG. 5C is observed.

On the other hand, FIG. 5D is a graph in which an example of a result of a preliminarily calculated variation of the luminance value of the pixel 13 by the phase addition method when the ultrasonic wave transmission beams 10-1 to 10-5 are transmitted is plotted.

In this case, as seen from a comparison between FIGS. 5C and 5D, luminance value variation characteristics illustrated in FIG. 5C are considerably different from those illustrated in FIG. 5D.

As described above, in a case of generating an ultrasonic image in a certain area by performing a plurality of ultrasonic wave transmission operations on a subject, a variation occurs in the luminance value of each pixel present in a certain area in an image generated in each ultrasonic wave transmission operation (the image is hereinafter referred to as a sub-frame). This actual variation of the luminance value is hereinafter referred to as a "luminance value variation".

In a case where a scattering substance is present in a pixel of interest, it can be estimated in advance how the luminance value in a sub-frame varies during the ultrasonic wave transmission operation by a calculation using a physical model representing ultrasonic wave transmission and reception characteristics. This variation of the luminance value estimated by the calculation is hereinafter referred to as a "sensitivity variation".

Further, it can be determined whether a scattering substance is present in a pixel of interest by comparing the luminance value variation with the sensitivity variation.

In this regard, the present inventors have conceived the idea of determining a target area and an area other than the target area in an ultrasonic image by the above-described method. This method makes it possible to accurately determine whether a target is present.

The present inventors have also conceived the idea of displaying an image representing a result of a determination as to whether a target area is present. Displaying such an image makes it possible to easily determine whether a target is present at a certain position in an image.

The present inventors have also conceived the idea of determining a target area by the above-described method and selectively extracting a target image from image data. More specifically, the present inventors have conceived the idea that, when a target is not present at a certain position, an image based on image data at the position is displayed with a luminance lower than a luminance corresponding to an image value at the position. The present inventors have also conceived the idea that, when a target is present at a certain position, an image is displayed in a state of emphasizing the luminance corresponding to the image value at the position. According to the image generation method described above, it is possible to provide a user with an image in which a target is emphasized. Displaying such an image allows the user to easily determine whether a target is present at a certain position.

The present inventors have also conceived the idea of displaying an image based on characteristic information indicating characteristics of a plurality of pieces of image data corresponding to a plurality of ultrasonic wave transmission operations. Displaying such characteristic information allows the user to easily determine whether a target is present at a certain position.

In the present exemplary embodiment, an example is described where ultrasonic image data is generated by the subject information acquisition apparatus. The configuration of the subject information acquisition apparatus and the information processing method according to the present exemplary embodiment will be described below.

FIG. 1 is a block diagram illustrating a configuration example of a processing apparatus 7 according to the present exemplary embodiment. The processing apparatus 7 illustrated in FIG. 1 includes a connection switch unit 701, which switches a connection state between a transmission/reception unit 6 and the processing apparatus 7, an ultrasonic wave transmission control unit 702, a signal reception unit 703, an information processing unit 704, and a control central processing unit (CPU) 705.

The ultrasonic wave transmission control unit 702 transmits an ultrasonic wave under control of the control CPU 705. The ultrasonic wave is transmitted from the transmission/reception unit 6. In addition, an ultrasonic wave signal reflected from a subject is received by the transmission/reception unit 6 and is converted into an analog electric signal.

Next, the signal reception unit 703 converts the analog electric signal derived from the ultrasonic wave signal output from the transmission/reception unit 6 into a digital signal.

The digital signal generated by the signal reception unit 703 is transferred to the information processing unit 704. The information processing unit 704, which serves as an image data acquisition unit, generates image data (ultrasonic image) based on the digital signal transferred from the signal reception unit 703.

The information processing unit 704 performs appropriate signal processing and image processing on the reflected wave of the ultrasonic wave. The processing will be described in detail below. With this configuration, not only phase addition processing on the acquired reception signal, but also image reconfiguration can be performed by applying any algorithm.

Typically, in a case of generating an ultrasonic image, phase addition is performed. In some cases, another image reconfiguration method to which an algorithm different from phase addition may be performed. Examples of another image reconfiguration method include back projection in a time domain or Fourier domain generally used for a tomography technique. In this way, not only phase addition processing, but also image reconfiguration processing to which any algorithm is applied may be applied.

With this configuration, an ultrasonic image can be acquired based on an ultrasonic wave reception signal. The information processing unit 704, which serves as the image data acquisition unit, may acquire image data by reading out image data (ultrasonic image) stored in an external server.

The control CPU 705 supplies data and control signals necessary for controlling each block.

In addition, the control CPU 705 supplies the ultrasonic wave transmission control unit 702 with waveform data and control signals for transmitting an ultrasonic wave. The control CPU 705 supplies the connection switch unit 701 with parameters for setting the connection state of the transmission/reception unit 6, the ultrasonic wave transmission control unit 702, and the signal reception unit 703 so that the ultrasonic wave transmission and reception operation is performed by selecting a desired element group in the probe array 601 present in the transmission/reception unit 6.

The control CPU 705 also supplies the signal reception unit 703 with control signals and parameters necessary for signal reception control.

The control CPU 705 also supplies the information processing unit 704 with control signals and parameters necessary for processing the digital signal transferred from the signal reception unit 703.

The information processing unit 704 generates an ultrasonic image by performing appropriate signal processing and image processing on the digital signal depending on the determination result.

A display apparatus 8 displays a photoacoustic image and an ultrasonic image, which are formed by the information processing unit 704, or an image obtained by superimposing the photoacoustic image and the ultrasonic image, and a user interface (UI) for operating the images and the apparatus. A liquid crystal display is generally used, However, any type of display, such as an organic electro luminescence (EL) display, may also be used.

Figure 2A:
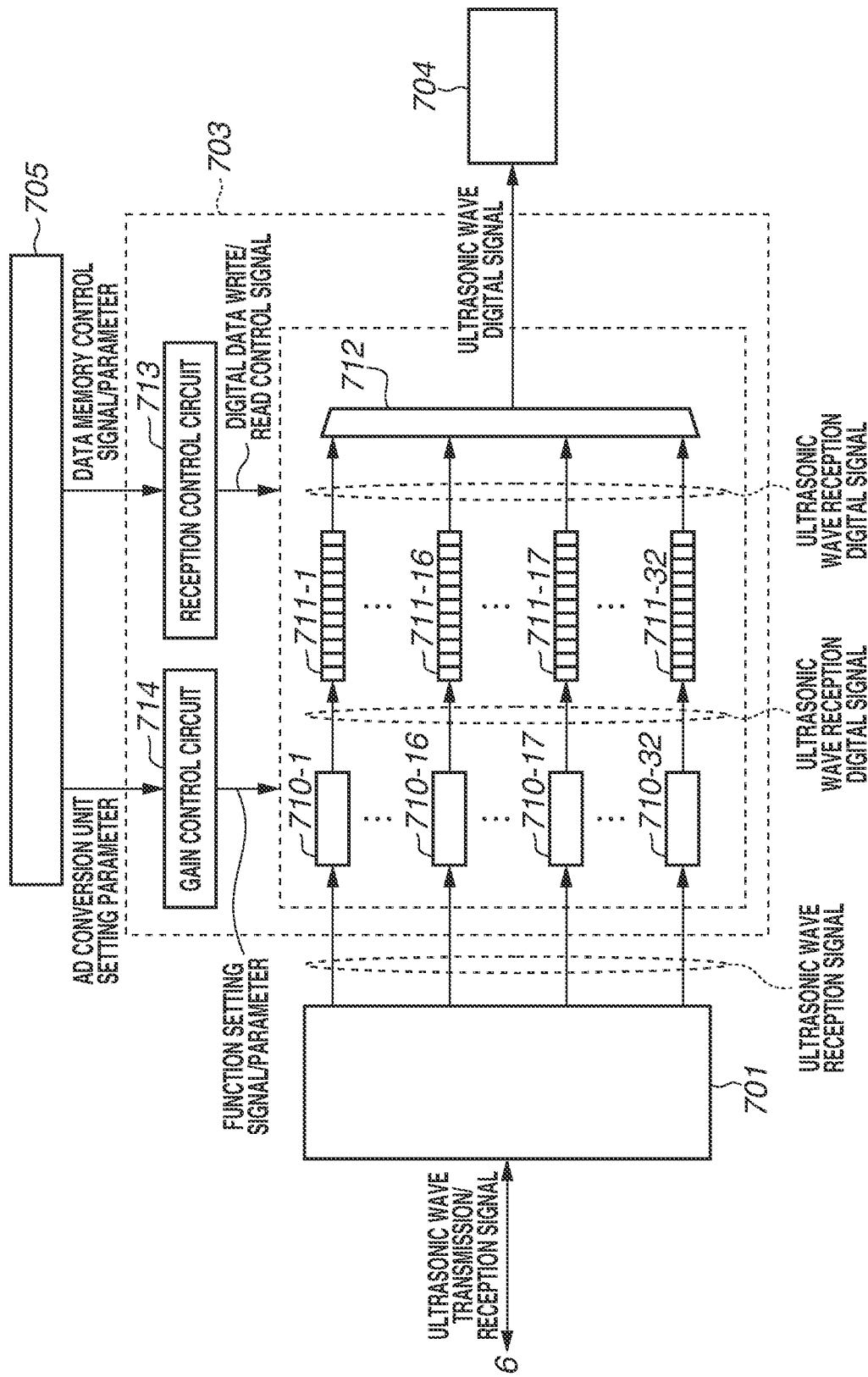
FIGS. 2A, 2B, 2C, and 2D are diagrams each illustrating a configuration of the processing apparatus according to the first exemplary embodiment.

FIG. 2A illustrates a configuration example of the signal reception unit 703 and a peripheral area thereof according to the present exemplary embodiment. FIG. 2A illustrates a case where the signal reception unit 703 is configured with 32 channels. However, the number of channels of the signal reception unit 703 is not limited to 32 channels and can be determined as appropriate depending on the specifications of the apparatus.

The signal reception unit 703 includes analog-to-digital (A/D) conversion units 710-1 to 710-32, data memories 711-1 to 711-32, a multiplexer 712, a reception control circuit 713, and a gain control circuit 714.

The ultrasonic wave signal acquired by the transmission/reception unit 6 and converted into the analog electric signal passes through the connection switch unit 701 and is converted into a digital signal in each of the A/D conversion units 710-1 to 710-32. In this case, the A/D conversion units 710-1 to 710-32 perform sampling of the ultrasonic wave signal by using a sampling clock that is generated in the processing apparatus 7 or is supplied from the outside of the processing apparatus 7. This sampling allows the A/D conversion units 710-1 to 710-32 to convert the analog electric signal into the digital signal. The A/D conversion units 710-1 to 710-32 are each supplied with an appropriate sampling clock from the inside of the processing apparatus 7 or from the outside of the processing apparatus 7 depending on the frequency hand of the acquired ultrasonic wave signal.

Depending on the performance of each of the A/D conversion units 710-1 to 710-32, a digital signal having a bit width in a range from about a 12-bit width to a 16-bit width are output from each of the A/D conversion units 710-1 to 710-32. The digital signal output from each of the A/D conversion units 710-1 to 710-32 is introduced into the corresponding one of the data memories 711-1 to 711-32 under control of the reception control circuit 713. Assume that the data memories 711-1 to 711-32 each have a capacity more than or equal to a capacity for storing digital signals corresponding to a maximum measurement depth in the subject.

Further, the gain control circuit 714 performs a gain control operation, such as a Time Gain Control (TGC) operation, on the A/D conversion units 710-1 to 710-32. For example, the TGC operation is performed based on a time when the ultrasonic wave echo reaches the transmission/reception unit 6, thereby obtaining an ultrasonic image with a uniform contrast.

The reception control circuit 713 performs a control operation to write digital signals output from the A/D conversion units 710-1 to 710-32 into the data memories 711-1 to 711-32, respectively. In addition, the reception control circuit 713 controls the multiplexer 712 to arbitrarily select the data memories 711-1 to 711-32, read out a digital signal from the selected data memory, and transfer the digital signal to the information processing unit 704. In many cases, the reception control circuit 713 sequentially selects all the data memories 711-1 to 711-32 one by one, reads out a digital signal from the selected data memory, and transfers the digital signal to the information processing unit 704.

The information processing unit 704 generates ultrasonic image data. An example where image data is generated when phase addition is applied as an image reconfiguration algorithm will be described below.

FIG. 6 illustrates an example of a positional relationship among the pixel 11 in a target sample area, the probe array 601, and the elements 601-M and 601-L of the probe array 601. The probe array 601 is present in the transmission/reception unit 6.

When coordinates $(X_i, Y_i, Z_i)$ of the pixel 11 and coordinates $(X_M, Y_M, Z_M)$ of the reception element 601-M are determined in a certain coordinate system, a distance E between the pixel 11 and the element 601-L can be easily obtained by the Pythagorean theorem.

When the coordinates $(X_i, Y_i, Z_i)$ of the pixel 11 and coordinates $(X_L, Y_L, Z_L)$ of the reception element 601-L are determined in a certain coordinate system, a distance D between the pixel 11 and the element 601-L can be easily obtained by the Pythagorean theorem.

A sum (D+E) of the distance E between the pixel 11 and the reception element 601-L in the array and the length D of the transmission element 601-M corresponds to an ultrasonic wave transmission distance. Accordingly, a time required for the ultrasonic wave signal derived from the pixel 11 to reach the reception element 601-L in the array, when the ultrasonic wave is transmitted, is calculated by dividing the distance (D+E) by a sound speed.

During a period of receiving the ultrasonic wave signal from the inside of the target sample area, the data memories 711-1 to 711-32 sequentially store digital signals derived from the ultrasonic wave signal in chronological order. In addition, the digital signals are stored in an address order in accordance with a certain rule, for example, based on an ultrasonic wave transmission start time.

In this way, the relationship becomes clear between an ultrasonic wave arrival time from the reception element 601-M in the array to the pixel 11, an ultrasonic wave arrival time from the pixel 11 to the reception element 601-L in the array, and an address at which each digital signal is stored in the data memories 711-1 to 711-32. Accordingly, based on this relationship, the address of the data memory in which digital data derived from a certain target pixel is stored can be specified. The information processing unit 704 extracts digital signals corresponding to 32 channels and are derived from the pixel 11 from among the digital signals read out from the data memories 711-1 to 711-32. Then, the information processing unit 704 multiplies each piece of data corresponding to 32 channels by an optimum window function weighting coefficient and adds the calculation results, thereby performing phase addition processing for 32 channels.

Further, when signal processing, such as filter processing, envelope demodulation, or logarithmic compression, is additionally performed on the phase addition result, ultrasonic image data obtained after phase addition is applied is generated.

The process of generating ultrasonic image data by applying phase addition as an image reconfiguration algorithm has been described above.

The reception control circuit 713 described above with reference to FIG. 2A needs not necessarily perform the process of sequentially selecting the data memories 711-1 to 711-32 one by one and reading out a digital signal from the selected data memory. As long as a data transfer unit for transferring data from the signal reception unit 703 to the information processing unit 704 allows, data stored in the plurality of data memories 711 may be read out in parallel and transferred to the information processing unit 704. Alternatively, data stored in all the data memories 711-1 to 711-32 may be read out in parallel and transferred to the information processing unit 704. With this configuration, the rate of data transfer from the signal reception unit 703 to the information processing unit 704 can be increased, which leads to a refinement or an improvement in the frame rate of an ultrasonic image.

In the case of sequentially selecting the data memories 711-1 to 711-32 and reading out a digital signal from the selected data memory, the order of selection is not limited to a constant order with a certain pattern and can be changed depending on the situation.

Next, a configuration of each A/D conversion unit 710 will be described. FIG. 2C illustrates a configuration example of the A/D conversion unit 710 according to the present exemplary embodiment of the present disclosure. The A/D conversion unit 710 is composed of an AD converter integrated circuit (IC) 750. The AD converter IC 750 may have a configuration in which a low noise amplifier (LNA) or a variable gain amplifier (VGA) is incorporated. With this configuration, the AD converter IC 750 can amplify a small ultrasonic wave signal and perform a TGC control operation, The gain control circuit 714 performs a setting for an amplification ratio of the LNA and a TGC control operation. Various functions, such as an anti-aliasing low pass filter, are incorporated in the AD converter IC 750. The reception control circuit 713 and the gain control circuit 714 perform various settings for the functions. This configuration prevents the circuit size of the A/D conversion unit 710 from being increased, so that a large number of channels can be mounted on the signal reception unit 703 in an aggregated manner. As a result, it is possible to acquire an ultrasonic wave signal while increasing the number of elements in the probe array 601 without increasing the size of the processing apparatus 7, and to generate an image with a refined or an improved resolution.

Figure 2B:
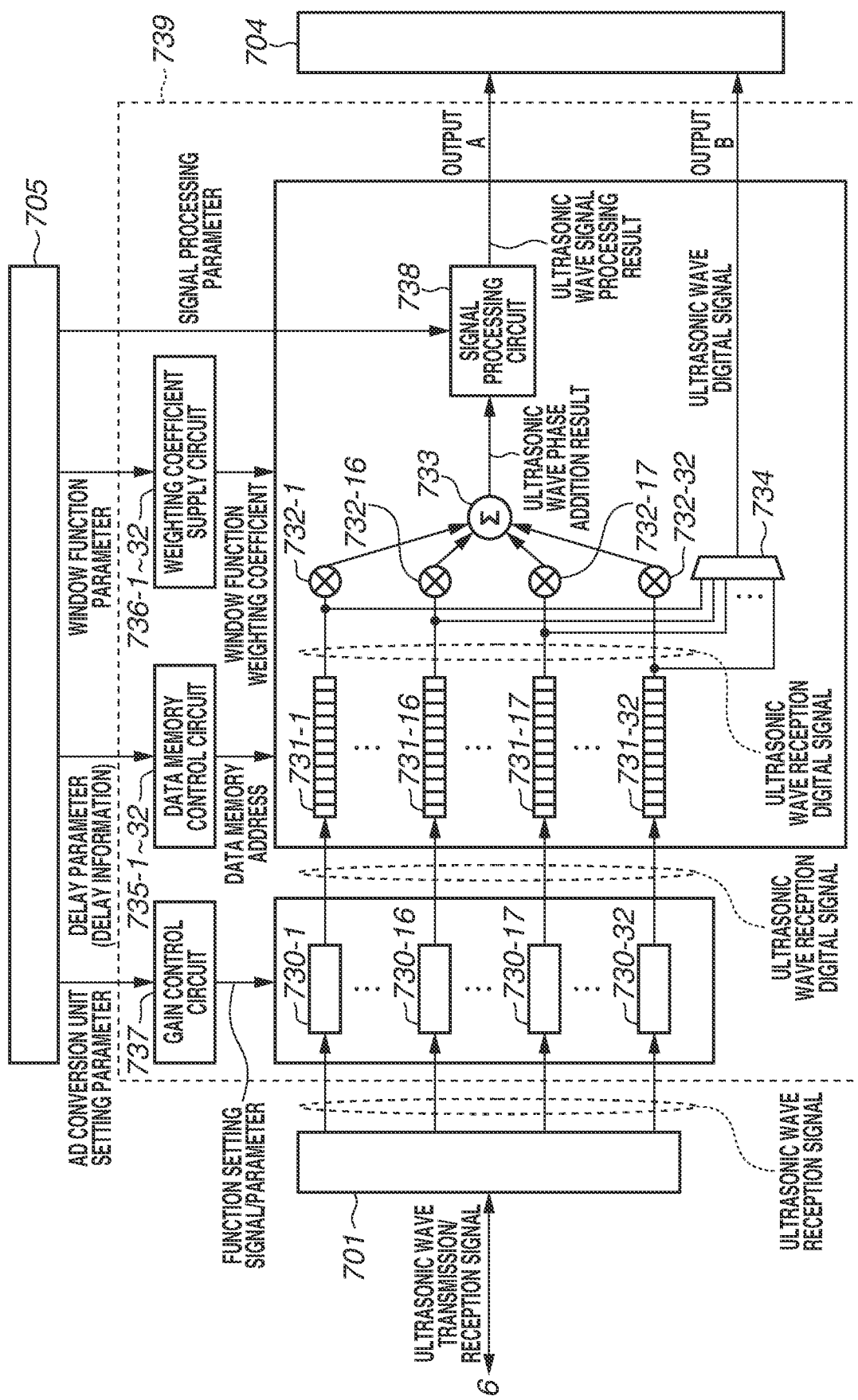
Figure 2C:
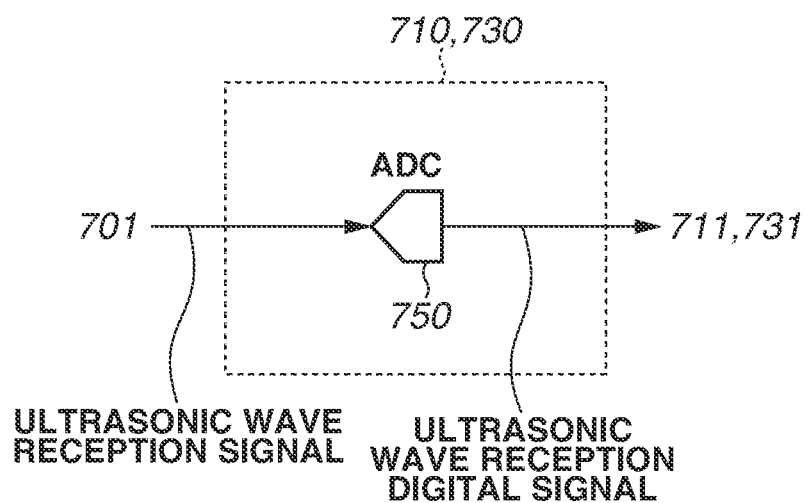
Figure 2D:
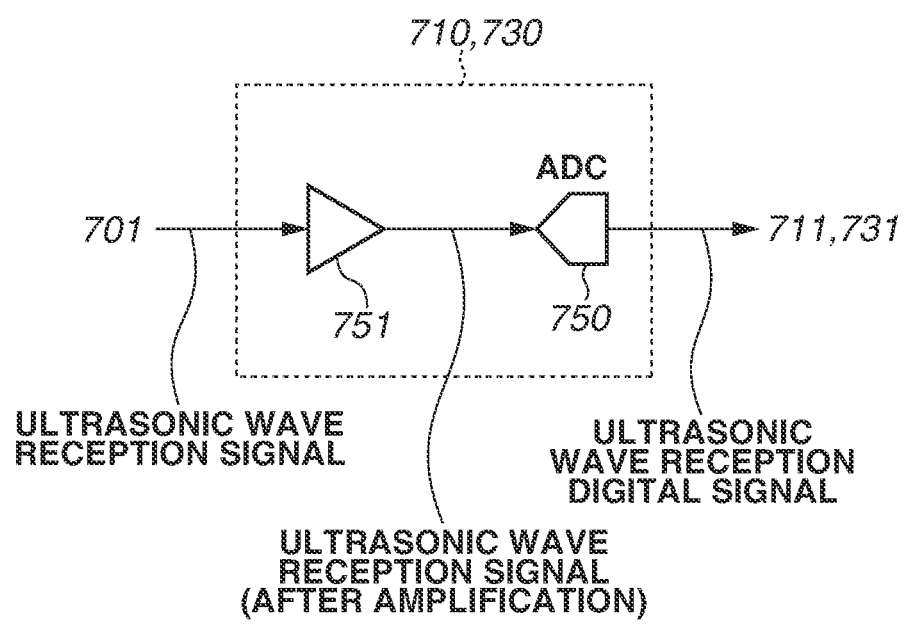

As illustrated in FIG. 2D, an LNA or VGA 751 may be disposed at a preceding-stage of the AD converter IC 750. A control operation for the LNA or VGA 751 may be performed by the gain control circuit 714.

The signal reception unit 703 illustrated in FIG. 2A can be replaced by a signal reception unit 739 illustrated in FIG. 2B. The configuration of the signal reception unit 739 will be described with reference to FIG. 2B.

FIG. 2B illustrates a configuration example of the signal reception unit 739 and a peripheral area thereof according to the present exemplary embodiment. FIG. 29 illustrates a case where the signal reception unit 739 is configured with 32 channels. However, the number of channels of the signal reception unit 739 is not limited to 32 channels and can be determined as appropriate depending on the specifications of the apparatus.

The signal reception unit 739 illustrated in FIG. 2B includes A/D conversion units 730-1 to 730-32, data memories 731-1 to 731-32, and a multiplexer 734. The signal reception unit 739 also includes apodization multipliers 732-1 to 732-32, an addition circuit 733, a signal processing circuit 738, data memory control circuits 735-1 to 735-32, and weighting coefficient supply circuits 736-1 to 736-32. The signal reception unit 739 also includes a gain control circuit 737.

The signal reception unit 739 can transfer digital signals derived from ultrasonic wave signals acquired by the data memories 731-1 to 731-32 to the information processing unit 704 through the multiplexer 734. A control operation for data transfer to the information processing unit 704 is performed by the data memory control circuits 735-1 to 735-32.

In addition, the signal reception unit 739 can acquire image data by performing phase addition using the apodization multipliers 732-1 to 732-32, the addition circuit 733, and the signal processing circuit 738. In this regard, the signal reception unit 739 differs from the signal reception unit 703 illustrated in FIG. 2A.

A method for acquiring image data by performing phase addition based on a reception signal will be described.

First, the data memory control circuits 735-1 to 735-32 each calculate an data memory address necessary for phase addition based on delay information supplied from the control CPU 705. Then, the data memory control circuits 735-1 to 735-32 supply the calculated data memory addresses to the data memories 731-1 to 731-32, respectively. Based on the data memory addresses supplied from the data memory control circuits 735-1 to 735-32, the digital data corresponding to a (arbitral) pixel 11 in the subject is read out from the data memories 731-1 to 731-32. Then, the read digital signals are output to the apodization multipliers 732-1 to 732-32, respectively. In this case, the digital signals with a same phase are output to the apodization multipliers 732-1 to 732-32, respectively.

The weighting coefficient supply circuits 736-1 to 736-32 supply the apodization multipliers 732-1 to 732-32 with window function weighting coefficients, respectively, based on the coordinates of any pixel 11 in the subject. The digital signals supplied to the apodization multipliers 732-1 to 732-32 are respectively provided with window function weighting coefficients calculated by the weighting coefficient supply circuits 736-1 to 736-32 for each channel, and are then output to the addition circuit 733. A Hanning function or a Hamming function can be suitably used as a window function. However, the window function is not limited to these examples, and a trapezoidal function may also be applied.

Further, the addition circuit 733 adds the digital signals with the same phase by the above-described processing, thereby performing phase addition for 32 channels.

The phase addition result is output to the signal processing circuit 738. The signal processing circuit 738 applies signal processing, such as filter processing, envelope demodulation, or logarithmic compression, to the phase addition result, and then transfers the processed data to the information processing unit 704.

The processing described above is performed on all target pixels in an observation area within the subject. As a result, phase addition processing data derived from all ultrasonic wave signals in a two-dimensional or three-dimensional observation area within the subject can be transferred to the information processing unit 704. The information processing unit 704 performs image processing on the phase addition processing data and generates ultrasonic image data. The generated ultrasonic image data is sent to the display apparatus 8 and is displayed as an image. At this point, the user can observe a two-dimensional or three-dimensional ultrasonic image in the subject.

Thus, in the signal reception unit 739 illustrated in FIG. 2C, after phase addition processing is performed on the ultrasonic wave signal output from the transmission/reception unit 6, the ultrasonic wave signal can be transferred to the information processing unit 704. In addition, image data can be generated by applying a signal processing algorithm other than phase addition to the ultrasonic wave signal output from the transmission/reception unit 6. In this case, the digital signals stored in the data memories 731-1 to 731-32 may be transferred to the information processing unit 704 through the multiplexer 734.

Employing the above-described configuration allows a single processing apparatus 7 to perform the ultrasonic wave transmission and reception operation. In addition, when phase addition is used as an algorithm, the signal reception unit 739 can perform phase addition processing, which reduces to eliminate the need for performing phase addition processing in the information processing unit 704. Accordingly, a signal processing load on the information processing unit 704 can be reduced. As a result, a time required for generating an ultrasonic image can be reduced. In particular, FIG. 2B illustrates the case where the signal reception unit 739 is configured with 32 channels. However, the beneficial effect becomes more prominent as the number of channels increases.

FIGS. 2C and 2D each illustrate a configuration example of the A/D conversion unit 730. A control operation for the AD converter IC 750 and the LNA or VGA 751 is performed by the gain control circuit 714. The control content is similar to that of the signal reception unit 703 illustrated in FIG. 2A.

Figure 3:
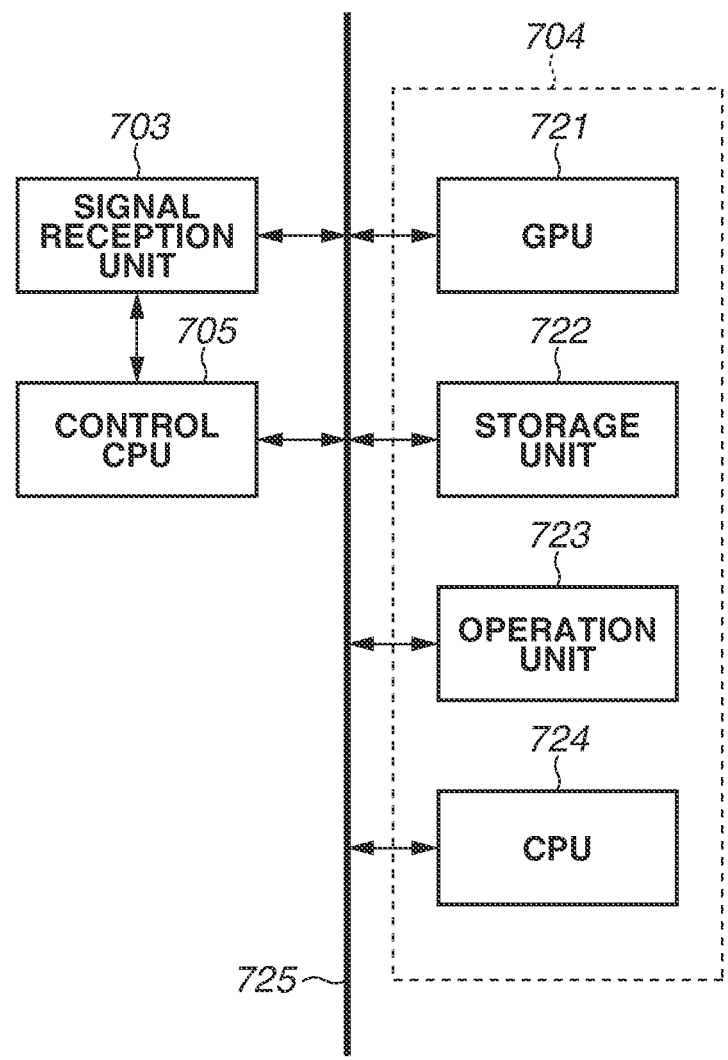
FIG. 3 is a block diagram illustrating a specific configuration example of the processing apparatus according to the first exemplary embodiment.

FIG. 3 is a block diagram illustrating a configuration example of the processing apparatus 7 according to the present exemplary embodiment. The information processing unit 704 illustrated in FIG. 3 includes an operation unit 723 for a user (mainly for an examiner such as a healthcare professional) to input instructions, such as a measurement start instruction, and parameters for measurement, to the apparatus. The information processing unit 704 also includes a graphics processing unit (GPU) 721 that forms an ultrasonic image from each of acquired ultrasonic wave signals. The information processing unit 704 further includes a CPU 724 that receives various operations from the user through the operation unit 723 to generate control information necessary for measurement operation, and controls each function through a system bus 725. The information processing unit 704 further includes a storage unit 722 that stores the digital signals transferred from the signal reception units 703 and 739 and setting information about the measurement operation.

The digital signals derived from the ultrasonic wave signals transferred from the signal reception units 703 and 739 are first stored in the storage unit 722 of the information processing unit 704.

The CPU 724 performs processing on the ultrasonic wave digital signals that are generated by the signal reception units 703 and 739 and are transferred to the storage unit 722. Examples of the processing include a sensitivity variation correction for the probe array 601, interpolation processing for elements physically or electrically lost, and filter processing for reducing noise. Further, the CPU 724 writes the processed digital signals into the storage unit 722. The digital signals subjected to processing by the CPU 724 and written into the storage unit 722 are used to generate an ultrasonic image by the GPU 721.

Further, the CPU 724 receives various requests, such as an image capturing start instruction and an image capturing interruption instruction, from the user through the operation unit 723, and manages the operation for acquiring subject information and controls each function through the system bus 725. The CPU 724 generates related control information based on parameters for acquiring subject information. For example, the CPU 724 outputs control information about the ultrasonic wave transmission and reception control operation, such as a plurality of focusing settings for ultrasonic beams, to the control CPU 705. The CPU 724 also outputs information about the TGC control for ultrasonic wave signals to the control CPU 705.

In addition, the CPU 724 manages identification information for identifying each apparatus, information uniquely set to each apparatus, and the apparatus state by monitoring the state of each piece of hardware.

The GPU 721 forms an ultrasonic image by converting information about a tissue in the subject into an image based on the ultrasonic wave data written in the storage unit 722. Information that is more suitable for diagnosis is formed by applying various correction processing, such as luminance adjustment, distortion correction, and clipping of an area of interest, to the formed image. Further, for example, parameters and display images for ultrasonic images are adjusted based on a user's operation on the operation unit 723.

Processing, such as noise reduction, on the ultrasonic wave digital signals transferred to the storage unit 722 may be performed instead of using the CPU 724, or in cooperation with the CPU 724.

An ultrasonic image is obtained by performing image reconfiguration processing on two-dimensional or three-dimensional ultrasonic wave digital signals that are detected and generated by a plurality of elements 601-L arranged in an array. As a result, subject information, such as a distribution of characteristics of an acoustic impedance or the like, can be visualized. Examples of the image reconfiguration processing to be used include back projection in a time domain or Fourier domain generally used for a tomography technique, and phase addition processing. Under less time pressure, an image reconfiguration technique, such as an inverse problem analysis method using repeated processing can be used, and subject information can be visualized using a probe including a reception focus function, such as an acoustic lens, without performing image reconfiguration processing.

The GPU 721 is configured using a GPU that generally includes a high-performance calculation processing function and a graphic display function, or the like. With this configuration, a time required for image reconfiguration processing and display image formation processing can be reduced.

The operation unit 723 is an input device used for the user to designate parameters related to a subject operation acquisition operation, such as a reception gain setting in the ultrasonic wave reception operation. The operation unit 723 includes an ultrasonic image luminance adjustment unit, and also includes a function for performing other image processing operations. In general, the operation unit 723 is composed of a mouse, a keyboard, a touch panel, and the like.

Using the processing apparatus 7 described in the first exemplary embodiment of the present disclosure allows the processing apparatus 7 to perform the ultrasonic wave transmission and reception operation. Accordingly, the entire apparatus can be downsized and produced at a low cost. In particular, FIGS. 2A and 2B illustrate the case where the signal reception units are configured with 32 channels. However, the beneficial effect becomes more prominent as the number of channels increases.

The display apparatus 8 may be provided separately from the subject information acquisition apparatus. The information processing unit 704 can transmit ultrasonic image data in a wired or wireless manner to the display apparatus 8.

As the operation unit 723, an operation console that can be operated by a user and is composed of a mouse, a keyboard, and the like can be used. The display apparatus 8 may he configured using a touch panel, and the display apparatus 8 may be used as the operation unit 723.

The display apparatus 8 may be configured to input, for example, information about a position or depth to he observed. As a method for inputting information, a value may be input, or information may be input by operating a slider bar. Alternatively, an image to be displayed on the display apparatus 8 may be updated depending on the input information. This configuration allows the user to set an appropriate parameter while checking the image generated based on the parameter determined by a user's operation.

The user may transmit information input via the operation unit 723 to the subject information acquisition apparatus via a network by operating the operation unit 723 that is provided remotely from the subject information acquisition apparatus.

The components of the subject information acquisition apparatus may be configured as separate devices, or may be configured as an integrated device. At least some of the components of the subject information acquisition apparatus may be integrated as one device.

Information to be transmitted and received between the components of the subject information acquisition apparatus is exchanged in a wired or wireless manner.

A scattering substance to be imaged is herein referred to as a target. A subject area that is not used as an imaging target, a subject area that is not observed is not called a target.

Next, an image display method including information processing according to the present exemplary embodiment will be described with reference to FIG. 7. Each process is executed in such a manner that the processing apparatus 7 controls the operation of each component of the subject information acquisition apparatus.

<Step S100: Process of Setting Control Parameter>

The user designates a control parameter for ultrasonic wave transmission conditions (e.g., a transmission beam shape, a transmission voltage, a transmission waveform, a repetition frequency, and elements to be used for transmission and reception) for the transmission/reception unit 6, which are necessary for acquiring subject information, by using the operation unit 723. The information processing unit 704 sets the control parameter determined based on a user's instruction.

<Step S200: Process of Installing Probe at Predetermined or Desired Position>

In a case of using a handheld type transmission/reception unit as the transmission/reception unit 6, the user installs the transmission/reception unit 6 at a desired position by gripping the transmission/reception unit 6. Alternatively, a drive unit (not illustrated) may move the transmission/reception unit 6 gripped by a mechanism (not illustrated) to a predetermined position.

<Step S300: Process of Transmitting Ultrasonic Wave>

The transmission/reception unit 6 transmits an ultrasonic wave to a subject based on the control parameter designated in step S100.

<Step S400: Process of Receiving Ultrasonic Wave>

The ultrasonic wave transmitted from the transmission/reception unit 6 is reflected inside the subject and received by the transmission/reception unit 6 as an ultrasonic echo signal.

The information processing unit 704 starts a signal collection operation based on the control parameter designated in step S100. More specifically, the information processing unit 704 performs amplification and AD conversion processing on the analog electric signal, which is derived from the ultrasonic echo signal and is output from the transmission/reception unit 6, thereby generating an amplified digital electric signal. The information processing unit 704 stores the digital electric signal in the storage unit 722 If image capturing using a plurality of sub-arrays per frame is designated in step S100, the processing in steps S200 to S400 are repeatedly executed on a designated sub-array to repeatedly perform the ultrasonic wave transmission and reception operation and the operation of generating a digital signal derived from the ultrasonic echo signal.

<Step S500: Process of Generating Ultrasonic Image Data>

The GPU 721 or the CPU 724 of the information processing unit 704 serving as the image data acquisition unit generates ultrasonic image data based on the digital electric signal data stored in the storage unit 722, and stores the generated ultrasonic image data in the storage unit 722. The information processing unit 704 serving as the image data acquisition unit may acquire image data by reading out image data (ultrasonic image) stored in an external server.

Further, target determination processing according to the present exemplary embodiment is also carried out in this process. This processing will be described in detail below.

<Step S600: Process of Generating and Displaying Image Based on Ultrasonic image Data>

The information processing unit 704, which serves as a display control unit, generates an image based on the ultrasonic image data obtained in step S500 and causes the display apparatus 8 to display the generated image. The image value of the image data may be directly used as the luminance value of the displayed image. Predetermined processing may be applied to the image value of the image data to determine the luminance of the displayed image.

To refine or improve the visibility of the generated ultrasonic image, any image processing may be performed on the ultrasonic image in the information processing unit 704 and then the ultrasonic image may be displayed on the display apparatus 8.

Next, a characteristic image generation method according to the present exemplary embodiment will be described with reference to a flowchart of an image generation method illustrated in FIG. 8.

<Step S510: Process of Combining B-mode Image Data for One Frame>

The information processing unit 704 serving as the image data acquisition unit combines pieces of ultrasonic image data of respective sub-frames (hereinafter referred to as a sub-frame image) generated from the digital electric signal data for each sub-frame obtained in steps S300 and S400, thereby generating a B-mode image for one frame. As a method for combining the image data, a simple addition may be used, or the image data may be multiplied by independent coefficients for each pixel of each sub-frame image and the calculation results may be added. After the addition, the image quality of the B-mode image may be optimized by dividing the image data by independent coefficients for each pixel of each sub-frame image.

Further, the image quality of the B-mode image may be optimized by performing independent processing, such as addition, subtraction, multiplication, or division, for each pixel. In any case, the method for optimizing the image quality of the B-mode image is not particularly limited.

<Step S520: Process of Selecting Determination Pixel>

The information processing unit 704 determines which one of the pixels 11 is selected as a pixel to be subjected to target determination processing in the ultrasonic image that forms one frame.

<Step S530: Process of Extracting Luminance Value Variation Pattern of Selected Pixel From Sub-Frame Image for One Frame>

The information processing unit 704 extracts data of the luminance value variation pattern corresponding to the selected pixel 11 from the sub-frame image generated to form one frame. The data of the luminance variation pattern corresponding to the pixel 11 corresponds to an image value sequence of a plurality of pieces of image data at a target position.

<Step S540: Process of Comparing Extracted Luminance Value Variation Pattern with Luminance Value Variation Pattern of Selected Pixel Calculated from Physical Model>

The information processing unit 704 serving as the template data acquisition unit calculates data of the sensitivity pattern corresponding to the selected pixel from a physical model, which represents ultrasonic wave transmission and reception characteristics, for each sub-frame image generated to form one frame. Alternatively, the information processing unit 704 serving as the template data acquisition unit acquires data indicating the sensitivity variation pattern calculated in advance. The sensitivity variation pattern calculated from the physical model representing ultrasonic wave transmission and reception characteristics is hereinafter referred to as a "sensitivity variation template". The data indicating the sensitivity variation pattern corresponding to the selected pixel corresponds to a template data sequence of a plurality of pieces of template data at the target position. In other words, the data indicating the sensitivity variation pattern corresponding to the selected pixel is template data in which a spatial sensitivity distribution of the subject information acquisition apparatus is reflected. The data indicating the sensitivity variation pattern corresponding to the selected pixel indicates an estimated value of an image value of data that can be generated when an ultrasonic scattering substance is present at the target position. An image value included in the image value sequence and template data included in the template data sequence are each associated with a common ultrasonic wave transmission and reception operation.

The information processing unit 704 may acquire a plurality of pieces of template data corresponding to a plurality of ultrasonic wave transmission and reception operations by assigning coordinates to predetermined template data based on relative position information indicating a relative position between the target position and the transmission/reception unit 6 in each of the plurality of ultrasonic wave transmission and reception operations. For example, the information processing unit 704 can generate the plurality of pieces of template data corresponding to the plurality of ultrasonic wave transmission and reception operations by defining coordinates while the spatial sensitivity distribution of the subject information acquisition apparatus is linked to the position of the transmission/reception unit 6 during the ultrasonic wave transmission and reception operation.

Further, the information processing unit 704 may acquire relative position information indicating a relative position between the target position and the transmission/reception unit 6 in the plurality of ultrasonic wave transmission and reception operations. Next, the information processing unit 704 may read out the template data corresponding to the relative position information from the storage unit 722 to thereby acquire the template data corresponding to the plurality of ultrasonic wave transmission and reception operations. In this case, a plurality of pieces of template data corresponding to a plurality of pieces of relative position information may be stored in the storage unit 722. If the template data corresponding to the acquired relative position information is not stored in the storage unit 722, new template data may be generated by interpolation processing using template data corresponding to relative position information in the vicinity of the acquired relative position information.

Further, the information processing unit 704, which serves as a similarity information acquisition unit, calculates a similarity between the actual luminance value variation pattern obtained in step S530 and the sensitivity variation pattern, and determines whether the target is present in the selected pixel based on the similarity. In the present exemplary embodiment, an example is described where a calculation of a correlation between the data on the luminance value variation pattern extracted in step S530 and the sensitivity variation template acquired in step S540 is used as a method for calculating the similarity in the determination as to whether the target is present. In addition to the correlation calculation, any index may be used as long as the index is information indicating the similarity.

The information processing unit 704 serving as the similarity information acquisition unit performs correlation calculation processing using the sensitivity variation template data and the luminance value variation pattern extracted from a plurality of sub-frame images. In this case, the information processing unit 704 performs a correlation value calculation as represented by the expression (6) using these pieces of data. The expression (6) indicates an example where the number of sub-frames is three.

$$Rvox1 = \frac{\sum_{i=1}^{3}(Pi \times \alpha i)}{\sqrt{\sum_{i=1}^{3} Pi^2} \times \sqrt{\sum_{i=1}^{3} \alpha i^2}} \quad (6)$$

Rvox1 represents the correlation value corresponding to the pixel 11. "i" represents the number given to each sub-frame and corresponds to the order of beams transmitted in one frame. $P_i$ represents the luminance value of the pixel 11 corresponding to an i-th ultrasonic wave transmission operation. $\alpha_i$ represents sensitivity variation template data on the pixel 11 corresponding to the i-th ultrasonic wave transmission operation.

More specifically, the information processing unit 704 serving as the similarity information acquisition unit calculates information indicating the correlation corresponding to the pixel 11 by using the luminance value of the pixel 11, the pixel 11, and the sensitivity variation template data. In this case, the information processing unit 704 calculates the correlation value corresponding to the pixel 11 by using a plurality of pieces of sensitivity variation template data corresponding to a respective plurality of ultrasonic wave transmission operations and luminance value variation data corresponding to a plurality of ultrasonic wave transmission operations.

When the expression (6) is generalized and correlation value data on a three-dimensional space is calculated from N sub-frames, a calculation as represented by the expression (7) is performed.

$$R(X, Y, Z) = \frac{\sum_{i=1}^{N}(P(X, Y, Z, i) \times \alpha(xi, yi, zi))}{\sqrt{\sum_{i=1}^{N} P(X, Y, Z, i)^2} \times \sqrt{\sum_{i=1}^{N} \alpha(X, Y, Z, i)^2}} \quad (7)$$

R(X, Y, Z) represents the result (correlation value in this case) the template calculation corresponding to the target position (X, Y, Z) of volume data. P(X, Y, Z, i) represents the luminance value of sub-frame image data corresponding to the i-th ultrasonic wave transmission operation corresponding to the target position (X, Y, Z) of ultrasonic image data. α(X, Y, Y) represents the value of the sensitivity variation template data corresponding to an i-th light irradiation corresponding to the target position (X, Y, Z) of ultrasonic image data. R(X, Y, Z) takes a value in a range from −1 to 1. If the coordinates of sub-frame data do not match the coordinates of sensitivity variation template data, coordinates of one of the pieces of data may be converted into coordinates of the other one of the pieces of data, or coordinates of both pieces of data may be replaced by new coordinates. In this case, a value at a certain coordinate may be replaced by a value at another coordinate, or the value at another coordinate may be calculated by interpolation. In other words, when ultrasonic image data at a specific position is focused, a correlation value between a luminance value sequence of a sub-frame image corresponding to the specific position and a sensitivity variation template data sequence corresponding to the specific position is calculated. Thus, the information processing unit 704 serving as the similarity information acquisition unit can acquire information indicating the correlation between a data sequence of luminance value variation data of a plurality of pieces of image data at a target position and a data sequence of a plurality of pieces of sensitivity variation template data at the target position.

Target determination processing is performed on the entire image capturing area, so that the target determination result (correlation value in this case) corresponding to the entire image capturing area can be obtained. A part of the image capturing area, or an area other than the image capturing area may be used as a template calculation target.

FIGS. 5A to 5D are graphs each illustrating a correspondence relationship between the luminance value variation pattern corresponding to the i-th ultrasonic wave transmission operation and the sensitivity variation template data.

For example, at a pixel in which the target is present, the luminance value variation pattern as illustrated in FIG. 5A is obtained and the sensitivity variation template as illustrated in FIG. 5B is obtained, As a result of comparing FIGS. 5A and 5B, it can be determined that the correlation value increases and thus the target is present. On the other hand, at a pixel in which the target is not present, for example, the luminance value variation pattern as illustrated in FIG. 5C is obtained and the sensitivity variation template as illustrated in FIG. 5D is obtained. As a result of comparing FIGS. 5C and 5D, it can be determined that the correlation value decreases and thus the target is not present.

In this way, the calculation using the sensitivity variation template data makes it possible to obtain information related to whether an absorbent is present in each pixel. In other words, information indicating the correlation corresponds to information indicating the possibility that the target is present.

<Step S550: Process of Checking whether all Designated Pixels are Selected>

The information processing unit 704 repeatedly performs the processing in steps S520, S530, and S540 until all the pixels designated as pixels on which target determination processing is performed are selected and the target determination processing is completed.

<Step S560: Process of Generating Determination Image Data for One Frame>

The information processing unit 704 generates determination image data by combining target determination results for all selected pixels.

Next, the information processing unit 704 serving as the display control unit may use the determination information acquired in step S560 to generate an image based on which whether the target is present can be determined, and may cause the display apparatus 8 to display the generated image.

The information processing unit 704 may perform image processing based on the determination information on image data to generate an image based on which whether the target is present can be determined, and may cause the display apparatus 8 to display the generated image. The information processing unit 704 may cause a display unit to selectively display image data corresponding to a position where the similarity satisfies a predetermined condition.

For example, the information processing unit 704 may perform amplification processing by multiplying a luminance value corresponding to an image value of a pixel corresponding to a position where the target is present by a coefficient that is greater than or equal to "1" based on the determination information. Further, the information processing unit 701 may perform attenuation processing by multiplying a luminance value corresponding to an image value of a pixel corresponding to a position where the target is not present by a coefficient that is less than "1" based on the determination information. In the attenuation processing, the luminance value corresponding to the image value of the corresponding pixel may be multiplied by "0" so that a portion other than the target area is set substantially as a non-display area.

Further, the information processing unit 704 may display the position where the target is present and the position where the target is not present by coloring the positions with different colors. In this case, the information processing unit 704 may display an image at the position where the target is present with a color of relatively high visibility, and may display an image at the position where the target is not present with a color of relatively low visibility.

Further, the information processing unit 704 may combine luminance value amplification/attenuation processing with color coding processing.

The information processing unit 704 may divide an image into three areas, i.e., a target area, an area other than the target area, and an area in the vicinity of a boundary between the target area and the area other than the target area, and may display the image so that the respective areas can be identified. In this case, the area in the vicinity of the boundary is a part of the target area or a part of the portion other than the target area.

For example, the information processing unit 704 may perform attenuation processing by multiplying a luminance value corresponding to an image value in the area in the vicinity of the boundary in the target area and the area other than the target area by a coefficient that is less than "1". The information processing unit 704 may perform amplification processing by multiplying a luminance value corresponding to an image value in the target area (except the area in the vicinity of the boundary) by a coefficient that is greater than or equal to "1", and may multiply the luminance value corresponding to the image value in the portion other than the target area by "0" so that the portion other than the target area can be set as the non-display area. This processing makes it possible to smoothly connect an image in the target area with an image in the area other than the target area. The three areas may be displayed with different colors.

While an example is described above where an image is displayed based on image data for one frame, the above-described image processing may be performed on a plurality of pieces of image data. For example, image data of a plurality of frames may be classified into some groups each including at least one piece of image data, and the image processing may be performed on partial combined image data generated as a result of performing combining processing on each group.

Further, the information processing unit 704 may perform parallel display, superimposed display, or alternate display of an image to which the above-described image processing is applied and an image to which the above-described image processing is not applied. For example, when the information processing unit 704 causes the display apparatus 8 to display the image to which the above-described image processing is not applied in step S600, the information processing unit 704 may switch the display to parallel display or superimposed display by receiving a display switch instruction from the user. Further, when the information processing unit 704 causes the display apparatus 8 to display the image to which the above-described image processing is not applied in step S600, the information processing unit 704 may switch the image to the image to which the above-described image processing is applied by receiving a display switch instruction from the user through the operation unit 723.

Further, the information processing unit 704 may cause the display apparatus 8 to display an image indicating characteristic information corresponding to a position designated by the user through the operation unit 723, together with the image based on the image data. In this case, a position where the image indicating the characteristic information is displayed may be designated based on an instruction for the image based on the image data displayed on the display apparatus 8.

Further, the information processing unit 704 may display a characteristic information image obtained by converting characteristic information corresponding to each of a plurality of pixels into an image. The information processing unit 704 may display a combined image of various types of different characteristic information images, or may display various types of characteristic information images in parallel, in a superimposed manner, or alternately. Further, the information processing unit 704 may perform attenuation processing by multiplying a characteristic information value, which is less than a certain threshold, in the target area and the area other than the target area of the characteristic information image by a coefficient that is less than "1", Further, the information processing unit 704 may perform amplification processing by multiplying a characteristic information value, which is greater than or equal to a certain threshold corresponding to an image value in the target area (except the area in the vicinity of the boundary) by a coefficient that is greater than or equal to "1", and may multiply the luminance value corresponding to the image value in the portion other than the target area by "0" so that the portion other than the target area can be set as the non-display area, The above-described processing makes it possible to smoothly connect the image in the target area with the image in the area other than the target area. Further, the three areas may be displayed with different colors.

The threshold used for determination of the target area and the area other than the target area may be bit set by the user or the subject information acquisition apparatus according to the present exemplary embodiment. The user may set the threshold through the operation unit 723 by using a slider bar, a dial, or the like.

The information processing unit 704 may display information (e.g., graph) indicating a variation of the luminance value as illustrated in FIGS. 5A to 5C.

According to the first exemplary embodiment of the present disclosure, it is possible to provide an image that allows a target area to be easily discriminated from a portion other than the target area. The user can easily determine whether a target (observation target) is present at a certain position in an image by checking the image displayed according to the present exemplary embodiment.

In the first exemplary embodiment of the present disclosure, the luminance variation pattern generated when electronic scanning is performed in each pixel to be subjected to target determination processing is calculated in a sub-frame direction and the calculated luminance variation pattern is used as a template.

A second exemplary embodiment of the present disclosure differs from the first exemplary embodiment of the present disclosure in that templates corresponding to sub-frame images, respectively, are individually generated and target determination processing is performed.

Figure 9A:
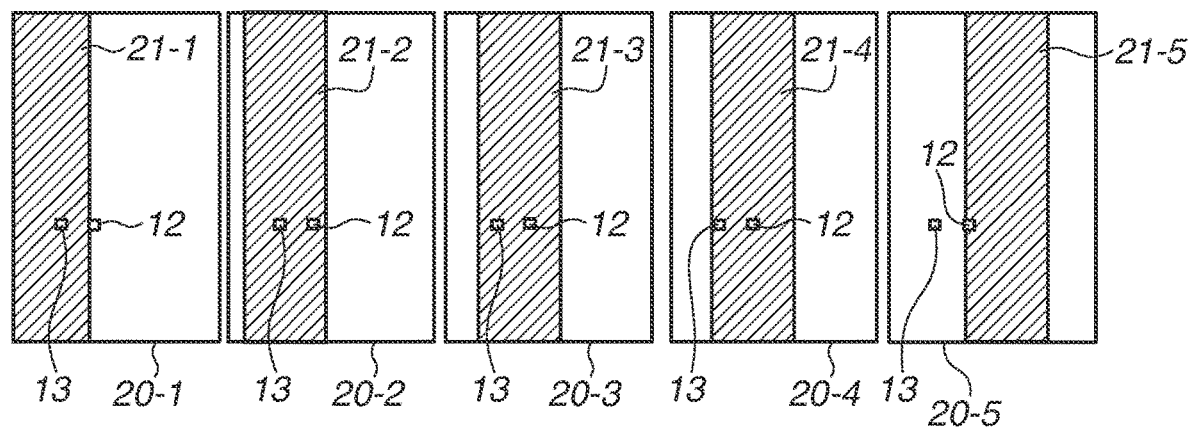
FIGS. 9A and 9B each illustrate another operation status in which an ultrasonic image is generated according to a second exemplary embodiment.

The second exemplary embodiment will be described in detail with reference to FIG. 9A, FIG. 9A illustrates sub-frame templates 20-1 to 20-5 respectively corresponding to sub-frames generated by beams 1 to 5 illustrated in FIG. 4 and used in the first exemplary embodiment described above.

In the sub-frame templates 20-1 to 20-5, sensitivity information is present in transmission beam areas 21-1 to 21-5 in which transmission beams as indicated by a shaded portion are distributed, and substantially no sensitivity information is present in an area other than the transmission beam areas 21-1 to 21-5.

In the second exemplary embodiment of the present disclosure, such sub-frame templates are prepared for all patterns of sub-frames that form one frame, and target determination processing is performed.

When the sensitivity information corresponding to the pixel 12 in each of the sub-frame templates 20-1 to 20-5 is plotted on the Y-axis and the beam numbers 1 to 5 are plotted on the X-axis, the same sensitivity variation template information as that illustrated in FIG. 5B can be obtained.

When the sensitivity information corresponding to the pixel 13 in each of the sub-frame templates 20-1 to 20-5 is plotted on the Y-axis and the beam numbers 1 to 5 are plotted on the X-axis, the same sensitivity variation template information as that illustrated in FIG. 5D can be obtained.

In the sub-frame templates, if it can be assumed that the sensitivity information in one sub-frame is the same or substantially the same as the sensitivity information in another sub-frame in a transmission beam area 21, the sensitivity information in the same transmission beam area 21 can be used. This configuration makes it possible to avoid redundancy due to the process in which the sensitivity information corresponding to the transmission beam area 21 is individually calculated for all sub-frames and stored. As a result, a reduction in calculation load and a reduction in required memory capacity can be achieved.

Figure 9B:
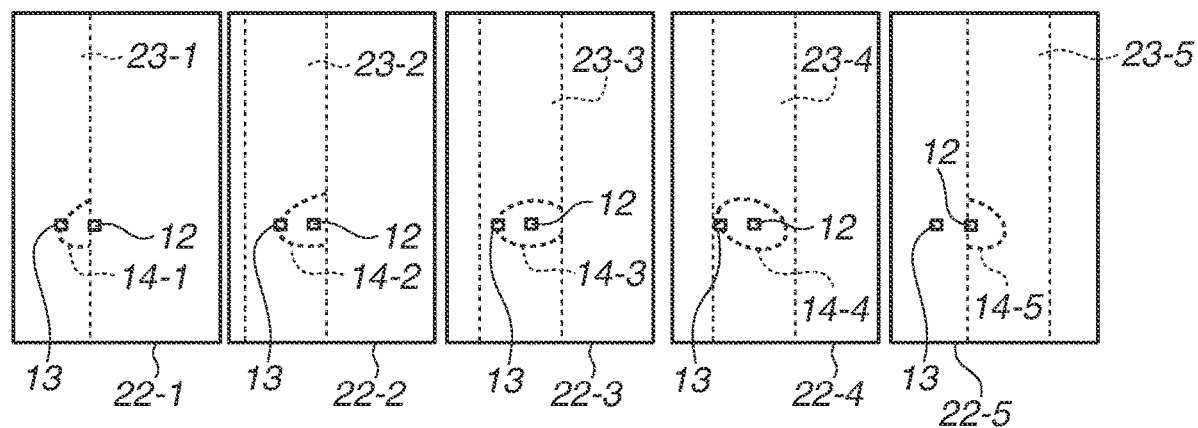

An example where a correlation calculation is performed using the sub-frame templates 20-1 to 20-5 will now be described with reference to FIGS. 9A and 9B. FIG. 9B illustrates sub-array B-mode images 22-1 to 22-5 generated for each sub-array when the target 11 is present at the same position as that illustrated in FIG. 4 in the probe array 601. The sub-array B-mode images 22-1 to 22-5 include images respectively corresponding to the transmission beam areas 21-1 to 21-5 in which transmission beams are distributed.

In the correlation calculation according to the second exemplary embodiment of the present disclosure, four types of calculations are performed. In a first calculation, pixel values having the same coordinates are multiplied using the sub-frame templates 20-1 to 20-5 and sub-frame templates 23-1 to 23-5 (calculation result (1)). In a second calculation, the pixel values of the sub-frame templates 20-1 to 20-5 are raised to the second power (calculation result (2)), In a third calculation, the pixel values of the sub-frame templates 23-1 to 23-5 are raised to the second power (calculation result (3)). In a fourth calculation, the calculations for obtaining the calculation result (1), the calculation result (2), and the calculation result (3) are performed on the pixels having the same coordinates. By the four types of calculations, the correlation value of a pixel group that forms one frame can be obtained.

In the calculation of raising the pixel values of the sub-frame templates 20-1 to 20-5 to the second power to obtain the calculation result (2), squared sub-frame templates (not illustrated) may be prepared in advance. This leads to a reduction in load on the square calculation.

On the other hand, the sensitivity variation template described in the first exemplary embodiment can be extracted from the sub-frame templates 20-1 to 20-5.

For example, when the value of the pixel 12 is acquired from each of the sub-frame templates 20-1 to 20-5 illustrated in FIG. 9A and the beam numbers are plotted on the X-axis and the value of the pixel 12 is plotted on the Y-axis, the graph illustrated in FIG. 5B is obtained. In other words, the sensitivity variation template for the pixel 12 is extracted.

Further, when the value of the pixel 13 is acquired from the sub-frame, templates 20-1 to 20-5 illustrated in FIG. 9A and the beam numbers are plotted on the X-axis and the value of the pixel 13 is plotted on the Y-axis, the graph illustrated in FIG. 5D is obtained. In other words, the sensitivity variation template for the pixel 13 is extracted.

When a sub-frame template group is preliminarily stored, in this way, in the subject information acquisition apparatus according to the present exemplary embodiment, the correlation calculation using the sensitivity variation template described in the first exemplary embodiment can also be performed. Storing the sub-frame template group in advance is beneficial in that the load on the calculation of the sensitivity variation template during target determination processing can be reduced.

According to the second exemplary embodiment of the present disclosure, it is possible to provide an image that allows a target area to be easily discriminated from a portion other than the target area. The user can easily determine whether a target (observation target) is present at a certain position in an image by checking the image displayed according to the present exemplary embodiment. In addition, the calculation load can be reduced and the target determination processing can be achieved.

A third exemplary embodiment of the present disclosure differs from the first and second exemplary embodiments of the present disclosure in that target determination processing on each pixel is performed using an artificial intelligence algorithm (machine learning algorithm or deep learning algorithm) that has learned a sensitivity variation template.

In the first and second exemplary embodiments of the present disclosure described above, an example is described where a sensitivity variation template corresponding to each pixel to be subjected to target determination processing is extracted.

In the third exemplary embodiment of the present disclosure, a learning data generation method of preparing one or more pieces of sensitivity variation template data for learning that are generated by superimposing one or more different noise patterns on a luminance value variation template of an ultrasonic image for one frame, may he employed. An artificial intelligence algorithm can be learned by comparing one or more pieces of sensitivity variation template data for learning with sensitivity variation template data on which no noise pattern is superimposed. The actual luminance value variation pattern in the sub-frame direction is input to the trained artificial intelligence algorithm generated as a result of the above-described processing, and then target determination processing is performed.

As an algorithm to be used, an algorithm configured using a neural network may be used. The algorithm to be used is not limited to a specific algorithm, as long as the algorithm is appropriate for target determination processing.

According to the third exemplary embodiment of the present disclosure, it is possible to provide an image that allows a target area to be easily discriminated from a portion other than the target area. The user can easily determine whether a target (observation target) is present at a certain position in an image by checking the image displayed according to the present exemplary embodiment.

The sub-frame templates described in the exemplary embodiments of the present disclosure are different depending on a beam profile of each transmission beam and the type of steering of each transmission beam. Accordingly, the sub-frame templates may be prepared depending on the transmission beam to be used, and the prepared sub-frame templates may be used for target determination processing.

For example, in a focused transmission beam, the contents of the sub-frame templates can be different depending on conditions such as a focus depth, a sound pressure for each transmission beam element, an apodization state, and a direction of transmitting the beam. In the case of transmitting a plane wave, the contents of the sub-frame templates can be different when the transmission direction of the plane wave is are different. The shape and characteristics of the transmission beam used for sub-frame template transmission are not particularly limited. The sub-frame template generation processing and the target determination processing can be performed regardless of the shape and characteristics of the transmission beam.

In addition, in the case of receiving an ultrasonic wave, the contents of the sub-frame templates can be different depending on how an opening of a probe used for reception is set. Further, the contents of the sub-frame templates can be different depending on how a TGC control pattern used for reception is set.

In the exemplary embodiments of the present disclosure, an example is described where sub-frame template data is generated with a scattering substance size that is the same as a pixel size. However, the sub-frame template data may be generated by setting a scattering substance size used for generating the sub-frame template data to be smaller than a pixel size. In this way, the target determination processing can be performed with a scattering substance size smaller than a pixel size.

Image data may be generated by extracting a portion, which is determined to be a target, from a result of generating a sub-frame template with a scattering substance size smaller than the resolution of the subject information acquisition apparatus according to the present exemplary embodiment and performing target determination processing, and the generated image data may be displayed alternately or displayed in a superimposed manner with the B-mode image. The image data obtained by extracting the portion determined to be the target may be displayed with a color. The target determination processing may be individually performed using the sub-frame template data generated using a plurality of scattering substance sizes, and the image data may be displayed in a superimposed manner with the B-mode image using different colors. Alternatively, the B-mode image and images indicating target determination processing results corresponding to a plurality of scattering substance sizes may be displayed alternately or continuously.

As the sub-frame templates, a transmission sound pressure distribution, a transmission directionality distribution, a reception directionality distribution, or a distribution of combinations of transmission and reception characteristics may be used.

In the exemplary embodiments of the present disclosure, an example is described where some of the elements of the probe array 601 are selected and used as a sub-array during the ultrasonic wave transmission operation. However, the exemplary embodiments of the present disclosure can also be applied to a case where ultrasonic images in the entire image capturing area are generated by performing the ultrasonic wave transmission operation using all the elements of the probe array 601. In this case, the target determination processing described in the exemplary embodiments of the present disclosure can also be performed using a plurality of ultrasonic image groups, which are obtained by changing an ultrasonic wave transmission mode, as sub-frame image groups.

In the exemplary embodiments of the present disclosure, an example is described where the target determination processing is performed by correlation processing using the luminance value variation pattern and the sensitivity variation template. However, the calculation mode is not limited to this example. The target determination processing may be performed based on a degree of proximity of a calculation result obtained by performing the same or different statistic calculation processing on each of the luminance value variation pattern and the sensitivity variation template. The "statistics calculation processing" referred to herein is not limited to a specific calculation, as long as the target determination processing can be appropriately performed. Examples of values obtained by the calculation processing include an average value, a deviation value, a standard deviation value, a variance value, a covariance value, a kurtosis, an entropy, an inner product value, an expectation value, a maximum value, a minimum value, an accumulation addition value, an addition count value, a multiplication value, a subtraction value, a division value, a value obtained by any combination of addition, subtraction, multiplication, and division, and a frequency value.

The present disclosure can also be carried out by executing the following processing. Specifically, software (program) for realizing the functions according to the exemplary embodiments described above is supplied to a system or apparatus via a network or various types of storage medium, and the program is read out and executed by a computer or a CPU, a micro processing unit (MPU), or the like in the system or apparatus.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may include one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The information processing apparatus according to the present disclosure allows easy determination of whether the possibility that a target (observation target) is present at a target position in an image is high.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2019-003584, filed Jan. 11, 2019, which is hereby incorporated by reference herein in its entirety.

What is claimed is:

1. An information processing apparatus comprising:
a processor and a memory coupled to each other and to perform operations including:
acquiring a plurality of pieces of image data generated by performing a plurality of ultrasonic wave transmission and reception operations on a subject, while changing an ultrasonic wave transmission and reception mode, acquiring a plurality of pieces of template data corresponding to the plurality of ultrasonic wave transmission and reception operations, respectively, and
acquiring information indicating a similarity between an image value sequence of the plurality of pieces of image data at a target position and a template data sequence of the plurality of pieces of template data at the target position,
wherein acquiring information includes calculating, as the acquired information indicating the similarity between the image value sequence and the template data sequence, a correlation based on the following expression (1):

$$R(X, Y, Z) = \frac{\sum_{i=1}^{N} (P(X, Y, Z, i) \times \alpha(xi, yi, zi))}{\sqrt{\sum_{i=1}^{N} P(X, Y, Z, i)^2} \times \sqrt{\sum_{i=1}^{N} \alpha(X, Y, Z, i)^2}} \quad (1)$$

where coordinates of the target position are represented by (X, Y, Z), a number of each of the plurality of ultrasonic wave transmission and reception operations is represented by i (i=1 to N), information indicating the correlation is represented by R, an image value included in the image value sequence is represented by P, and template data included in the template data sequence is represented by α.

2. The information processing apparatus according to claim 1, wherein each of the plurality of pieces of template data is template data in which a spatial sensitivity distribution of a subject information acquisition apparatus configured to execute the plurality of ultrasonic wave transmission and reception operations is reflected.

3. The information processing apparatus according to claim 1, wherein each of the plurality of pieces of template data is an estimated value indicating an image value of image data to be generated in a case where an ultrasonic scattering substance is present at the target position in each of the plurality of ultrasonic wave transmission and reception operations.

4. The information processing apparatus according to claim 1, wherein acquiring the plurality of pieces of template data includes assigning coordinates to predetermined template data based on relative position information indicating a relative position between the target position and array configured to receive an ultrasonic echo signal in the plurality of ultrasonic wave transmission and reception operations.

5. The information processing apparatus according to claim 1, wherein acquiring the plurality of pieces of template data includes acquiring relative position information indicating a relative position between the target position and an array configured to receive an ultrasonic echo signal in the plurality of ultrasonic wave transmission and reception operations and by reading out template data corresponding to the relative position information from a storage.

6. The information processing apparatus according to claim 1, wherein an image value included in the image value sequence and template data included in the template data sequence are each associated with a common ultrasonic wave transmission and reception operation.

7. The information processing apparatus according to claim 1, further comprising a display controller configured to cause a display to display an image based on the acquired information indicating the similarity between the image value sequence and the template data sequence.

8. The information processing apparatus according to claim 1, wherein acquiring the plurality of pieces of image data includes generating combined image data by combining the plurality of pieces of image data, and generating weighted combined image data by weighting the combined image data by using the acquired information indicating the similarity between the image value sequence and the template data sequence.

9. The information processing apparatus according to claim 8, further comprising a display controller configured to cause a display unit to display an image based on the weighted combined image data.

10. The information processing apparatus according to claim 1, further comprising a display controller,
wherein acquiring the plurality of pieces of image data includes generating combined image data by combining the plurality of pieces of image data, and
wherein the display controller is configured to cause a display to selectively display combined image data corresponding to a position where the similarity between the image value sequence and the template data sequence satisfies a predetermined condition.

11. The information processing apparatus according to claim 1, wherein each of the plurality of pieces of image data is image data generated so as to vary an ultrasonic wave transmission position or an ultrasonic wave reception position in each of the plurality of ultrasonic wave transmission and reception operations.

12. The information processing apparatus according to claim 1, wherein each of the plurality of pieces of template data includes template data generated by changing a size of a scattering substance with respect to an ultrasonic wave.

13. The information processing apparatus according to claim 1, wherein, in the ultrasonic wave transmission and reception mode, the plurality of ultrasonic wave transmission and reception operations are different in one of an ultrasonic wave transmission beam focusing mode, an ultrasonic wave reception beam focusing mode, and an ultrasonic wave transmission direction.

14. A method for an information processing apparatus, the method comprising:
acquiring a plurality of pieces of image data generated by performing a plurality of ultrasonic wave transmission and reception operations on a subject, while changing an ultrasonic wave transmission and reception mode;
acquiring a plurality of pieces of template data corresponding to the plurality of ultrasonic wave transmission and reception operations, respectively; and
acquiring information indicating a similarity between an image value sequence of the plurality of pieces of image data at a target position and a template data sequence of the plurality of pieces of template data at the target position,
wherein acquiring information includes calculating, as the acquired information indicating the similarity between the image value sequence and the template data sequence, a correlation based on the following expression (1):

$$R(X, Y, Z) = \frac{\sum_{i=1}^{N} (P(X, Y, Z, i) \times \alpha(xi, yi, zi))}{\sqrt{\sum_{i=1}^{N} P(X, Y, Z, i)^2} \times \sqrt{\sum_{i=1}^{N} \alpha(X, Y, Z, i)^2}} \quad (1)$$

where coordinates of the target position are represented by (X, Y, Z), a number of each of the plurality of ultrasonic wave transmission and reception operations is represented by i (i=1 to N), information indicating the correlation is represented by R, an image value included in the image value sequence is represented by P, and template data included in the template data sequence is represented by a.

15. A non-transitory computer-readable storage medium storing a program to cause a computer to perform a method for an information processing apparatus, the method comprising:
acquiring a plurality of pieces of image data generated by performing a plurality of ultrasonic wave transmission and reception operations on a subject, while changing an ultrasonic wave transmission and reception mode;
acquiring a plurality of pieces of template data corresponding to the plurality of ultrasonic wave transmission and reception operations, respectively; and
acquiring information indicating a similarity between an image value sequence of the plurality of pieces of image data at a target position and a template data sequence of the plurality of pieces of template data at the target position,
wherein acquiring information includes calculating, as the acquired information indicating the similarity between the image value sequence and the template data sequence, a correlation based on the following expression (1):

$$R(X, Y, Z) = \frac{\sum_{i=1}^{N}(P(X, Y, Z, i) \times \alpha(xi, yi, zi))}{\sqrt{\sum_{i=1}^{N} P(X, Y, Z, i)^2} \times \sqrt{\sum_{i=1}^{N} \alpha(X, Y, Z, i)^2}} \quad (1)$$

where coordinates of the target position are represented by (X, Y, Z), a number of each of the plurality of ultrasonic wave transmission and reception operations is represented by i (i=1 to N), information indicating the correlation is represented by R, an image value included in the image value sequence is represented by P, and template data included in the template data sequence is represented by α.

\* \* \* \* \*